(12) United States Patent
Stehr et al.

(10) Patent No.: US 9,382,583 B2
(45) Date of Patent: Jul. 5, 2016

(54) METHOD FOR THE AMPLIFICATION OF NUCLEIC ACIDS USING HEAT TRANSFER FOR NANOPARTICLES

(71) Applicant: GNA Biosolutions GmbH, Planegg (DE)

(72) Inventors: Joachim Stehr, Munich (DE); Federico Buersgens, Munich (DE); Lars Ullerich, Munich (DE)

(73) Assignee: GNA Biosolutions GmbH, Planegg (DE)

( * ) Notice: Subject to any disclaimer, the term of this patent is extended or adjusted under 35 U.S.C. 154(b) by 0 days.

(21) Appl. No.: 14/375,946

(22) PCT Filed: Feb. 1, 2013

(86) PCT No.: PCT/EP2013/052100
§ 371 (c)(1),
(2) Date: Jul. 31, 2014

(87) PCT Pub. No.: WO2013/113910
PCT Pub. Date: Aug. 8, 2013

(65) Prior Publication Data
US 2014/0377764 A1 Dec. 25, 2014

(30) Foreign Application Priority Data
Feb. 1, 2012 (DE) .......................... 10 2012 201 475

(51) Int. Cl.
C12P 19/34 (2006.01)
C12Q 1/68 (2006.01)

(52) U.S. Cl.
CPC ............. *C12Q 1/686* (2013.01); *C12Q 1/6844* (2013.01)

(58) Field of Classification Search
USPC ............................................... 435/6.12, 91.2
See application file for complete search history.

(56) References Cited

U.S. PATENT DOCUMENTS

| 7,998,672 | B2 | 8/2011 | Roper |
| 2002/0061588 | A1 | 5/2002 | Jacobson et al. |
| 2005/0026146 | A1 | 2/2005 | Frizsche et al. |
| 2005/0191651 | A1* | 9/2005 | Franzen et al. .................. 435/6 |
| 2010/0291696 | A1 | 11/2010 | Stehr et al. |
| 2011/0008797 | A1 | 1/2011 | Zilch et al. |

FOREIGN PATENT DOCUMENTS

| DE | 102007027654 | 12/2011 |
| EP | 1840222 | 10/2007 |
| EP | 2481817 | 8/2012 |
| WO | 0248399 | 6/2002 |
| WO | 2007143034 | 12/2007 |
| WO | 2009115335 | 9/2009 |

OTHER PUBLICATIONS

Li, M., et al., Enhancing the efficiency of a PCR using gold nanoparticles, Nucleic Acids Research, Nov. 27, 2005, vol. 33, No. 21, e184 (10 pages).
Stehr, J., et al., Gold NanoStoves for Microsecond DNA Melting Analysis, Nano Letters, 2008, vol. 8, No. 2, pp. 619-623.
Li, D., et al., Negligible absorption of radiofrequency radiation by colloidal gold nanoparticles, Journal of Colloid and Interface Science, Jan. 22, 2011, vol. 358, pp. 47-53.
Keblinski, P., et al., Limits of localized heating by electromagnetically excited nanoparticles, Journal of Applied Physics, Sep. 6, 2006, vol. 100, 054305 (pp. 1-5).
Hanson, G.W., et al., Electromagnetic absorption mechanisms in metal nanospheres: Bulk and surface effects in radiofrequency-terahertz heating of nanoparticles, Journal of Applied Physics, Jun. 22, 2011, vol. 109, 124306 (pp. 1-6).
Hamad-Schifferli, K., et al., Remote electronic control of DNA hybridization through inductive coupling to an attached metal nanocrystal antenna, Nature, Jan. 10, 2002, vol. 415, pp. 152-155.
Bellizzi, G., et al., On the Energy Transfer Between the Electromagnetic Field and Nanomachines for Biological Applciations, Bioelectromagnetics, Jan. 25, 2008, vol. 29, pp. 331-339.
Hu et al., Heat dissipation in gold-silica core-shell nanoparticles, Chemical Physics Letters, 372 (2003) 767-772. Mar. 20, 2003.
Baffou, G., et al., Femtosecond-pulsed optical heating of gold nanoparticles, Phys. Rev. B 84, 2011, 035415, 13 pages.

* cited by examiner

*Primary Examiner* — Kenneth Horlick
(74) *Attorney, Agent, or Firm* — Hodgson Russ LLP

(57) ABSTRACT

A method for the amplification of nucleic acids, in which nanoparticles in a reaction volume transfer heat to their environment through excitation. The method comprises a step of providing nanoparticles with the nucleic acids in a reaction volume and one or more heating steps. In at least one of the heating steps, the heating is achieved at least partially through the excitation of the nanoparticles. The interval of the excitation is chosen to be shorter or equal to a critical excitation time.

15 Claims, 17 Drawing Sheets

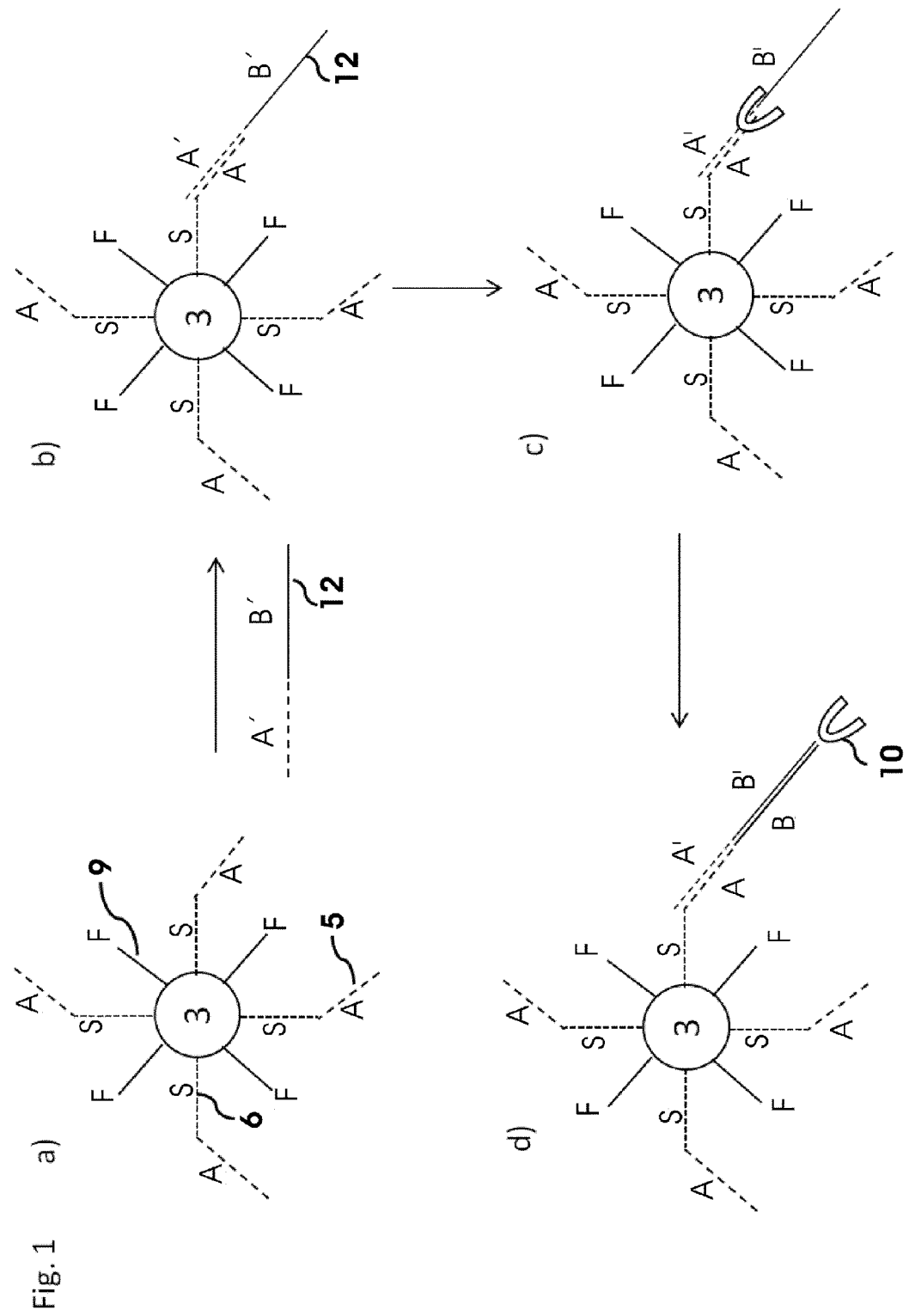

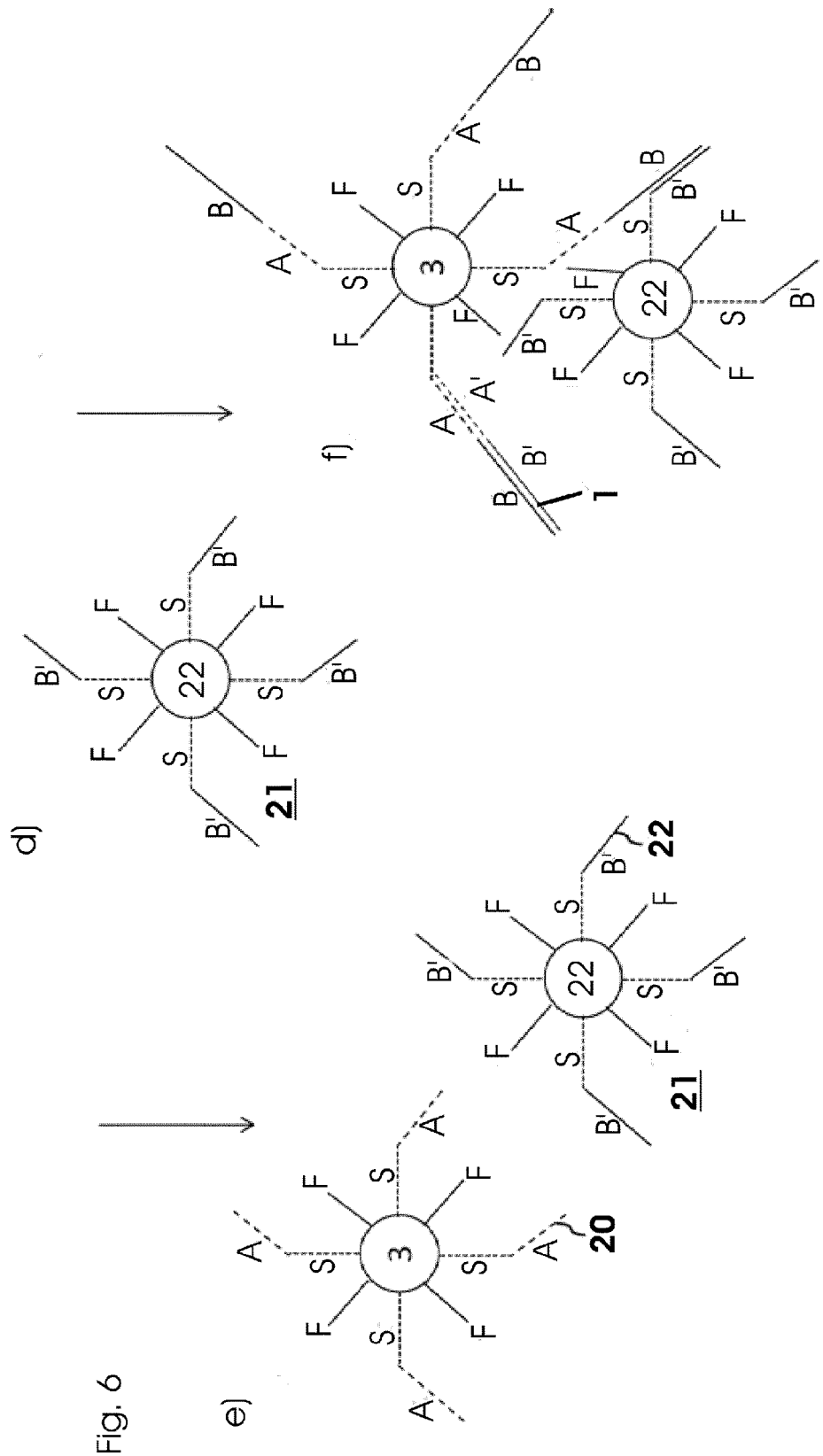

SEQUENCE LISTING

<160> NUMBER OF SEQ ID NOS: 10

<210> SEQ ID NO 1
<211> LENGTH: 65
<212> TYPE: DNA
<213> ORGANISM: artificial sequences
<220> FEATURE:
<221> NAME/KEY: source
<222> LOCATION: 1..65
<223> OTHER INFORMATION: /mol_type="DNA"
      /note="5' thiol modif. oligonucleotide ID1"
      /organism="artificial sequences"

<400> SEQUENCE: 1
aaaaaaaaaa aaaaaaaaaa aaaaaaaaaa aaaaagataa gataatgtag tccctggcct    60
caaag                                                                 65

<210> SEQ ID NO 2
<211> LENGTH: 25
<212> TYPE: DNA
<213> ORGANISM: artificial sequences
<220> FEATURE:
<221> NAME/KEY: source
<222> LOCATION: 1..25
<223> OTHER INFORMATION: /mol_type="DNA"
      /note="5' thiol modif. oligonucleotide ID2"
      /organism="artificial sequences"

<400> SEQUENCE: 2
aaaaaaaaaa aaaaaaaaaa aaaaa                                           25

<210> SEQ ID NO 3
<211> LENGTH: 53
<212> TYPE: DNA
<213> ORGANISM: artificial sequences
<220> FEATURE:
<221> NAME/KEY: source
<222> LOCATION: 1..53
<223> OTHER INFORMATION: /mol_type="DNA"
      /note="oligonucleotide ID3"
      /organism="artificial sequences"

<400> SEQUENCE: 3
atgcaaccta aggaggagag ttcctttgag gccagggact acattatctt atc            53

<210> SEQ ID NO 4
<211> LENGTH: 30
<212> TYPE: DNA
<213> ORGANISM: artificial sequences
<220> FEATURE:
<221> NAME/KEY: source
<222> LOCATION: 1..30
<223> OTHER INFORMATION: /mol_type="DNA"
      /note="oligonucleotide ID4"
      /organism="artificial sequences"

<400> SEQUENCE: 4
gttgtcttat agcattggtg ccgatttggg                                      30

<210> SEQ ID NO 5
<211> LENGTH: 65
<212> TYPE: DNA
<213> ORGANISM: artificial sequences
<220> FEATURE:
<221> NAME/KEY: source
<222> LOCATION: 1..65
<223> OTHER INFORMATION: /mol_type="DNA"
      /note="5' thiol modif. oligonucleotide ID5"
      /organism="artificial sequences"

```
<400> SEQUENCE: 5
aaaaaaaaaa aaaaaaaaaa aaaaaaaaaa aaaaaataca aatgcaacct aaggaggaga    60
gttcc                                                                65

<210> SEQ ID NO 6
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type="DNA"
      /note="oligonucleotide ID6"
      /organism="artificial sequences"

<400> SEQUENCE: 6
atgcaaccta aggaggagag ttcc                                           24

<210> SEQ ID NO 7
<211> LENGTH: 33
<212> TYPE: DNA
<213> ORGANISM: artificial sequences
<220> FEATURE:
<221> NAME/KEY: source
<222> LOCATION: 1..33
<223> OTHER INFORMATION: /mol_type="DNA"
      /note="5' thiol modif. oligonucleotide ID7"
      /organism="artificial sequences"

<400> SEQUENCE: 7
aaaaaaaaaa aaaaaaaaaa aaaaagggac tac                                 33

<210> SEQ ID NO 8
<211> LENGTH: 30
<212> TYPE: DNA
<213> ORGANISM: artificial sequences
<220> FEATURE:
<221> NAME/KEY: source
<222> LOCATION: 1..30
<223> OTHER INFORMATION: /mol_type="DNA"
      /note="oligonucleotide ID8"
      /organism="artificial sequences"

<400> SEQUENCE: 8
gataagataa tgtagtccct ggcctcaaag                                     30

<210> SEQ ID NO 9
<211> LENGTH: 44
<212> TYPE: DNA
<213> ORGANISM: artificial sequences
<220> FEATURE:
<221> NAME/KEY: source
<222> LOCATION: 1..44
<223> OTHER INFORMATION: /mol_type="DNA"
      /note="5' thiol modif. oligonucleotide ID9"
      /organism="artificial sequences"

<400> SEQUENCE: 9
aaaaaaaaaa aaaaaaaaaa aaaaagataa gataatgtag tccc                     44

<210> SEQ ID NO 10
<211> LENGTH: 65
<212> TYPE: DNA
<213> ORGANISM: artificial sequences
<220> FEATURE:
<221> NAME/KEY: source
<222> LOCATION: 1..65
```

```
<223> OTHER INFORMATION: /mol_type="DNA"
      /note="5' dithiol modif. oligonucleotide ID10"
      /organism="artificial sequences"

<400> SEQUENCE: 10
aaaaaaaaaa aaaaaaaaaa aaaaaaaaaa aaaaagataa gataatgtag tccctggcct    60
caaag                                                                65
```

METHOD FOR THE AMPLIFICATION OF NUCLEIC ACIDS USING HEAT TRANSFER FOR NANOPARTICLES

FIELD OF THE INVENTION

The invention concerns a method for the amplification of nucleic acids.

BACKGROUND OF THE INVENTION

Methods for the amplification of nucleic acids are known in the art. The patent specification U.S. Pat. No. 4,683,202 discloses a process for amplifying a specific nucleic acid sequence contained in a nucleic acid or a mixture of nucleic acids, wherein each nucleic acid consists of two separate complementary strands, of equal or unequal length. The process comprises: (a) treating the strands with two oligonucleotide primers, for each different specific sequence being amplified, under conditions such that for each different sequence being amplified an extension product of each primer is synthesised which is complementary to each nucleic acid strand, wherein said primers are selected so as to be sufficiently complementary to different strands of each specific sequence such that the extension product synthesised from one primer, when it is separated from its complement, can serve as a template for synthesis of the extension product of the other primer; (b) separating the primer extension products from the templates on which they were synthesised to produce single-stranded molecules; and (c) treating the single-stranded molecules generated from step (b) with the primers of step (a) under conditions that a primer extension product is synthesised using each of the single strands produced in step (b) as a template. The steps can be carried out consecutively or simultaneously. Furthermore, the steps (b) and (c) can be repeated until the desired extent of sequence amplification has been achieved. In the case that in the process the steps (a) and (c) are performed using a polymerase, the process is commonly referred to as polymerase chain reaction (PCR).

The international patent application WO 2007/143034 A1 discloses methods, which are supposedly suitable for the execution of PCR. The methods may comprise the use of an optical source to provide heating in a PCR. The methods may also include the use of surface plasmon resonance or fluorescence resonance energy transfer to allow real-time monitoring of a PCR reaction. The methods may comprise immobilising a template, primer or polymerase on a surface such as a gold or on another surface plasmon resonance active surface.

The patent application US 2002/0061588 A1 discloses methods for rendering nucleic acids locally and directly responsive to an external signal. The signal acts exclusively on one or several specific, localised parts of the nucleic acid. According to the invention, the signal can change the properties of a specific nucleic acid and thereby modify its function. Thus, the invention provides methods, which control the structure and function of a nucleic acid in a biological sample without influencing other parts of the sample. In one embodiment, a modulator transfers heat to a nucleic acid or a part of a nucleic acid, which results, e.g., in a destabilisation of inter- or intramolecular bonds and in an alteration of structure and stability of the nucleic acid. Preferred modulators include metal nanoparticles, semiconducting nanoparticles, magnetic nanoparticles, oxide nanoparticles and chromophores. It is also suggested, to use these methods in conjunction with PCR. Particularly, it is proposed to control a PCR reaction with a modulator.

The patent application US 2003/0143604 A1 concerns the use of nanoparticle detection probes to monitor amplification reactions, in particular PCR. Especially, the patent application deals with the use of nanoparticle oligonucleotide conjugates treated with a protective agent such as bovine serum albumin in order to quantitatively and qualitatively detect a target polynucleotide. The patent application discloses a nucleic acid amplification and detection using gold nanoparticle primers. In a first step, the nucleic acid target is denatured in the presence of the gold nanoparticles that are functionalised with primers. In a second step, the gold nanoparticles and the oligonucleotides attached thereto hybridise with the nucleic acid target and a copy of the complementary DNA sequence is produced starting from the nucleic acid primers, which are attached to the nanoparticles. The steps one and two are repeated and the optical signal, which is created by the binding of amplified complementary nanoparticle probes, is detected.

PROBLEM ACCORDING TO THE INVENTION

The underlying problem of the invention is to provide an improved method for the amplification of nucleic acids.

SOLUTION ACCORDING TO THE INVENTION

The problem is solved by a method with the features of claim 1. The method serves to amplify nucleic acids, wherein in a reaction volume, nanoparticles transfer heat to their environment through excitation.

The reaction volume is the volume, in which the method according to the invention is performed. The volume can be surrounded by a reaction vessel. The reaction volume contains a sample. The sample contains a liquid, preferably water. The nucleic acids, which can be amplified by the method, can be contained in the sample.

The nanoparticles according to the invention are preferably particles, which, due to their size, show special optical properties, particularly characteristic absorption or scattering spectra, that are not observed or not as distinct in the bulk material. Preferably, the nanoparticles have a diameter of between 2 and 500 nm, more preferably between 3 and 300 nm and most preferably between 5 and 200 nm. Preferred nanoparticles have a diameter between 7 and 150 nm. The nanoparticles can be spherical, however, non-globular shapes are also possible, e.g., elongated nanoparticles (nanorods). In a preferred embodiment of the invention, the nanoparticle comprises at least one semiconductor or one metal, preferably a noble metal, e.g., gold or silver. In one embodiment, the nanoparticle consists of metal entirely, in another embodiment the metal forms only one part of the nanoparticle, e.g., its shell. A preferred nanoparticle can be a shell-core nanoparticle. A preferred nanoparticle can possess pores on its surface, which pores can be occupied by atoms or molecules with a size and charge defined by the properties of the pores, particularly preferably, such atoms or molecules are only adsorbed to the nanoparticle when the nanoparticle is situated in a solution. According to the invention, the nanoparticle also comprises the atoms and molecules adsorbed to its surface. Due to their material absorption or plasmon resonance, preferred nanoparticles are suitable for absorbing optical energy.

When—through the excitation of a nanoparticle—heat is transferred from the nanoparticle to its environment, this means—according to the invention—that energy is transferred to the nanoparticle, wherein the nanoparticle heats its environment through the transfer of the energy. In this, preferentially, through the excitation, the immediate environment is heated more strongly than the wider environment of the nanoparticles. Typically, the nanoparticles are first heated through excitation and then transfer heat to their environment. It is also conceivable that through the excitation of the nanoparticles, heat is transferred to their environment without the nanoparticles themselves being heated first. Preferably, the environment of the nanoparticles is a spherical volume, which has a diameter equal to 100 times the diameter of the nanoparticle which is situated in the centre of the volume; more preferably the volume has 10 times, most preferably 4 times and preferably less than 2 times the diameter of the nanoparticle in its centre.

Preferably, through the excitation of the nanoparticles, the environment of the nanoparticles is heated locally. Especially fast changes in temperature are possible if the heated volume is only a fraction of the entire volume. On the one hand, a high temperature difference can be produced with only a small amount of energy input. On the other hand, a rapid cooling of the heated volume is possible if a sufficiently large cold temperature reservoir is present in the irradiated volume, such that after the irradiation of the nanoparticles, their environment is cooled down. This can be achieved by irradiating the nanoparticles sufficiently strongly (to gain the desired temperature increase) and for a sufficiently short amount of time (for the heat to remain localised).

Local heating according to the invention is thus present if the interval t of the excitation in the individual volume irradiated (e.g., in the focus of the laser) is chosen to be shorter or equal to a critical excitation interval t1. Here, t1 is the time which the heat requires to diffuse from one nanoparticle to the next at a mean nanoparticle distance, multiplied with a scaling factor s1; if |x| is the mean nanoparticle distance and the thermal diffusivity of the medium between the nanoparticles is D then t1 is given by $t1=(s1*|x|)^2/D$, wherein the thermal diffusivity D typically has a value of $D=10^{-7}$ m$^2$/s in aqueous solution.

The scaling factor s1 is a measure for how far the warm front of a particle spreads during the excitation interval. The temperature increase caused by an excited nanoparticle at a distance of a few nanoparticle diameters is only a very small fraction of the maximal temperature increase at the particle surface. In one embodiment of the invention, an overlap of the warm fronts of a few nanoparticles is permitted in the sense that for the definition of the critical excitation interval t1 according to the equation above, a scaling factor greater than 1 is used. In another embodiment of the invention, no overlap of the warm fronts is permitted during the excitation interval (corresponds to a markedly local heating) in the sense that for the definition of the critical excitation interval t1 according to the above equation, a scaling factor s1 less than or equal to 1 is used. For the definition of the local heating according to the invention, preferably s1=100, preferably s1=30, preferably s1=10, preferably s1=7, preferably s1=3 and most preferably s1=1, preferably, s1=0.7, preferably s1=0.3.

Values for s1>1 can be advantageous in such cases (amongst others), in which the irradiated volume shows a high aspect ratio (e.g., in the focus of a moderately focussed laser beam), such that comparatively many nanoparticles are situated at the surface of the irradiated volume and therefore, fewer heated nanoparticles are present in their environment and a marked heat efflux from the irradiated volume takes place, such that the heating contribution of the neighbours further away remains negligible for a longer period of time.

This means that, e.g., at a nanoparticle concentration of 1 nM, which results in a mean nanoparticle distance of |x|=1.2 µm, a local heating according to the invention takes place if the excitation interval remains shorter than t1=14 µs (the scaling factor is chosen as s1=1, $D=10^{-7}$ m$^2$/s). It can be assumed that when t is chosen to be t>t1 that the heat given off by the nanoparticles can—during irradiation—cover a distance by diffusion, which is greater than the mean particle distance, which in effect leads to an overlap of the warm fronts of many nanoparticles, such that there is a temperature increase in the entire volume between the nanoparticles; the temperature increase in the irradiated volume will be spatially the more homogeneous the longer the heating takes place, as an influence on the temperature distribution around a nanoparticle is not only exerted by the closest nanoparticles, but also by the neighbours further away.

If the reaction volume is irradiated with a radiation absorbed by the nanoparticles for longer than t1, the heating is termed as global.

A global heating according to the invention can, e.g., be carried out by heating the reaction volume from the outside with a Peltier element or a resistance heater. The global heating can also take place, e.g., by irradiating the reaction volume with radiation, which is absorbed by water more strongly than or equally strongly as by the nanoparticles. Here, the term temperature increase means the difference in the temperature at one location at the time of observation immediately after the excitation and the temperature at the same location immediately before the excitation.

Global heating and local heating can be carried out simultaneously.

Known methods for the amplification of nucleic acids comprise one or several steps, in which at least parts of the sample are required to be heated.

The invention makes it achievable that in the method for the amplification of nucleic acids, not the entire reaction volume needs to be heated. On the contrary, it is possible to only heat specific parts of the reaction volume through the excitation of nanoparticles. Advantageously, in such way, it becomes possible to only heat those parts of the reaction volume, which need to be heated for the amplification of the nucleic acids. Thus, heat sensitive parts of the sample can be preserved. The local heating can be faster than the global heating of the entire reaction volume, if less energy needs to be transferred. Therefore, advantageously, the invention makes it possible to provide a method for the amplification of nucleic acids, which is faster and requires less energy.

PREFERRED EMBODIMENTS ACCORDING TO THE INVENTION

A nucleic acid can be amplified by a polymerase chain reaction (PCR), in particular. The PCR is carried out in the reaction volume. The reaction volume contains one nucleic acid to be amplified, which is termed the original. The original is a single strand. In the reaction volume, the original can form a double strand together with its complementary strand, which is termed the complement. If the original and the complement are present as a double strand, this double strand must be denatured in a first step, i.e., the double strand must be split into two single strands. Melting is another term for denaturing. Denaturing occurs at a temperature, which is termed denaturing temperature. The reaction volume further contains at least two oligonucleotides, which are called primers. One of the primers is termed forward primer, the other is called reverse primer. The forward primer is complementary to the 3'-end of the original. The reverse primer is complementary to the 3'-end of the complement. In a second step, the forward primer hybridises with the original and the reverse primer hybridises with the complement. The hybridisation of the primers with the complementary parts of the original or the complement, respectively, is termed annealing. The second step takes place at a temperature, which is termed annealing temperature. The reaction volume further contains a DNA polymerase. In a third step, the DNA polymerase synthesises a copy of the complement starting from the forward primer. Starting from the reverse primer, the DNA polymerase synthesises a copy of the original. Through the synthesis, the copy of the complement is hybridised with the original and the copy of the original is hybridised with the complement. The third step is termed elongation and is carried out at a temperature called elongation temperature. After that, the first, second and third step are cyclically repeated until the desired extent of amplification is achieved, wherein the copy of the original is the original and the copy of the complement is the complement. If the original is situated on a DNA single strand that is longer than the original, then the PCR does not only produce copies of the original, but also copies of the said DNA single strand, which are longer in the 3' direction and contain the original. Accordingly, in this case, the PCR does not only produce copies of the complement, but also copies of the DNA single strand complementary to the said DNA single strand, wherein the copies are longer in the 3' direction and contain the complement.

As the separate steps of the PCR can be carried out at different temperature, it can be necessary to perform one or several heating steps and—where applicable—cooling steps during or between the steps of the PCR, in which heating and cooling steps the reaction volume or parts thereof are heated or cooled, respectively. Preferably, the heating in the heating step or in at least one of the heating steps is achieved at least partially through the excitation of the nanoparticles and the heating is preferably a local heating.

In the PCR, the denaturing temperature is preferably chosen such that the single strands of the DNA melt while not damaging the DNA polymerase in a significant way. A typical value for the denaturing temperature is, e.g., 95° C. The optimal annealing temperature usually depends on the sequence and length of the primers. Typically, primers are designed for the annealing temperature to be between 50° C. and 65° C. The optimal elongation temperature typically depends on the DNA polymerase used. When using Taq polymerase, e.g., typically, an elongation temperature of 72° C. is chosen.

Hybridisation in the sense of the present invention means the forming of a double strand from two single strands, each of which may consist of a nucleic acid and/or oligonucleotide. Under appropriate reaction conditions, the hybridisation typically leads to the lowest energy state, which can be achieved by the two single strands bonding to each other. This means, in other words, that under the appropriate conditions, the two single strands bind to each other in such a way that referring to the sequences of the two single strands, the greatest possible complementarity is produced.

When a nucleic acid A is partially complementary to a nucleic acid B, this means that one part of the nucleic acid A is complementary to one part of the nucleic acid B.

The excitation of the nanoparticles preferably takes place by means of an alternating field, more preferably by an alternating electromagnetic field, most preferably optically. Preferably, the excitation occurs in the range between far infrared and far ultraviolet light (in a range from 100 nm to 30 μm wavelength), more preferably in the range from near infrared to near ultraviolet light (in a range from 200 nm to 3 μm wavelength), most preferably in the visible light range (in a range of 400 nm to 800 nm). Compared to the conventional global heating of the reaction vessel from the outside, this may offer the advantage that the thermally insulating wall of the reaction vessel does not need to be overcome as the energy is transferred directly onto the nanoparticles. In this way, a faster heating of the desired parts of the sample can be achieved.

In a preferred embodiment of the invention, the nanoparticles are excited by a laser. More preferably, the laser light has a frequency, which excites the surface plasmon resonance of the nanoparticles. The laser can supply the light continuously or as pulsed light. The laser can, e.g., be a gas laser, a diode laser or a diode-pumped solid state laser. The time interval, in which the laser excites the nanoparticles in the irradiated volume, is preferably in the area of picoseconds to seconds, more preferably between nanoseconds and seconds and most preferably between 10 ns and 500 μs. Preferably, the excitation interval is shorter than the mean time needed for the heat, which arises in the environment of the nanoparticles, to diffuse across the mean nanoparticle distance, such that there is, on average, no significant overlap of the warm fronts of neighbouring particles. More preferably, the excitation interval is chosen for the temperature increase around each irradiated nanoparticle to drop to, on average, less than half its maximum in a distance of 20 nanoparticle diameters, more preferably in a distance of 2 nanoparticle diameters and most preferably in a distance of 1 nanoparticle diameter. In one embodiment, a short irradiation period of the laser per volume is preferable, such that a dehybridised DNA single strand can only diffuse away from the nanoparticle by less than 100 nm, more preferably by less than 20 nm during the denaturation. Thereby, the probability for the dehybridised DNA single strand to bind to an oligonucleotide on the same nanoparticle is high. This can lead to an acceleration of the method according to the invention. In a preferred embodiment, the concentration of the primer conjugated nanoparticles is smaller than 10 nM, wherein the excitation interval is preferably between 1 ns and 10 μs, more preferably between 10 ns and 1 μs and most preferably between 15 ns and 300 ns. The excitation interval is preferably not chosen to be significantly smaller than 1 ns; otherwise the heating period of the DNA double strand is not sufficient for the single strands contained therein to sufficiently separate by diffusion such that they will not immediately rehybridise to each other.

The duty cycle is the ratio of the excitation interval to the duration of the PCR cycle. The duty cycle is preferably chosen to be large enough for the excitation to lead to a sufficient denaturation of the DNA double strands by local heating. At the same time, the duty cycle is chosen to be such that the mean temperature increase of the entire sample is kept sufficiently small to avoid disturbances on the hybridisation, elongation and denaturation. Preferably, the duty cycle for the irradiated volume is less than 50%, more preferably less than 20% and most preferably less than 1%. The duty cycle in the irradiated volume is preferably greater than $10^{-12}$, more preferably greater than $10^{-10}$, more preferably greater than $10^{-9}$ and most preferably greater than $10^{-8}$. The surface power densities, with which the nanoparticles are excited, are preferably between 20 W/mm$^2$ and 1000 kW/mm$^2$, more preferably between 100 W/mm$^2$ and 100 kW/mm$^2$ and most preferably between 250 W/mm$^2$ and 10 kW/mm$^2$.

In another preferred embodiment, the energy of the laser light is transferred to the nanoparticles due to their material absorption. The light, which is used for the excitation of the nanoparticles, can also originate from, e.g., a thermic radiator, e.g., a flash bulb. In another preferred embodiment of the invention, the nanoparticles are excited through an alternating electromagnetic field or electromagnetic waves, which induce eddy currents in the nanoparticles. Appropriately designed nanoparticles can also be excited by ultrasound.

The term oligonucleotide in connection with the present invention preferably comprises not only (deoxy)oligoribonucleotides, but also oligonucleotides that contain one or more nucleotide analogues with modifications on their backbone (e.g. methylphosphonates, phosphothioates or peptide nucleic acids [PNA]), in particular on a sugar of the backbone (e.g. 2'-O-alkyl derivatives, 3'- and/or 5'-aminoriboses, locked nucleic acids [LNA], hexitol nucleic acids, Morpholinos, glycol nucleic acids (GNA), threose nucleic acid (TNA) or tricyclo-DNA; in this regard see the publication by D. Renneberg and C. J. Leumann entitled "Watson-Crick basepairing properties of Tricyclo-DNA", J. Am. Chem. Soc., 2002, Vol. 124, pages 5993-6002, the related content of which forms part of the present disclosure by way of reference) or contain base analogues, e.g., 7-deazapurine or universal bases such as nitroindole or modified natural bases such as N4-ethylcytosine. In one embodiment of the invention, the oligonucleotides are conjugates or chimeras with non-nucleosidic analogues, e.g. PNA. In one embodiment, the oligonucleotides contain, at one or more positions, non-nucleosidic units such as spacers, e.g. hexaethyleneglycol or $C_n$-spacers, where n is between 3 and 6. To the extent that the oligonucleotides contain modifications, these are chosen in such a way that a hybridisation with natural DNA/RNA analytes is also possible with the modification. Preferred modifications influence the melting behaviour, preferably the melting temperature, in particular in order to distinguish hybrids having differing degrees of complementarity of their amino acids (mismatch discrimination). Preferred modifications include LNA, 8-aza-7-deaza-purine, 5-propinyluracil, 5-propinylcytosine and/or abasic interruptions in the oligonucleotide. Further modifications according to the invention are, e.g., modifications with biotin, thiol and fluorescence donor and fluorescence acceptor molecules.

In a preferred embodiment of the invention, the nanoparticles are conjugated with oligonucleotides. In this way, the nanoparticles form nanoparticle oligonucleotide conjugates. In this manner, it can be achieved that oligonucleotides forming part of the method according to the invention can be specifically heated through the excitation of the nanoparticles without having to heat the reaction volume as a whole. In an especially preferred embodiment, the nanoparticles are conjugated to primers. More preferably, the nanoparticles are conjugated to the forward and reverse primers of the PCR. In a preferred embodiment of the invention, one kind of nanoparticle oligonucleotide conjugates have forward primers but no reverse primers attached; another kind has reverse but no forward primers attached.

In another preferred embodiment of the invention, one kind of nanoparticle oligonucleotide conjugates is conjugated with forward as well as reverse primers. In this embodiment, a new DNA single strand complementary to the original is synthesised in a PCR starting from the forward primer on a nanoparticle. This new DNA single strand is conjugated to the nanoparticle as the new DNA single strand contains the forward primer. Immediately after the synthesis, the new DNA single strand forms a double strand with the original. In a subsequent denaturation step, the new DNA single strand is separated from the original. At an annealing temperature, the new DNA single strand hybridises to a reverse primer, which is situated on the surface of the nanoparticle, such that a loop is formed. For the hybridisation with the reverse primer on the same nanoparticle, only a short distance has to be crossed. To achieve hybridisation with a reverse primer on a different nanoparticle at preferred nanoparticle concentrations, on average, the distance to be crossed is greater. Thus, in this embodiment, it is advantageously achievable that the annealing occurs more rapidly and that the PCR can be completed more quickly.

In a preferred embodiment of the invention, the nanoparticles are connected to the primers in such a way that covalent bonds with more than one thiol between primers and nanoparticles are present. Generally, PCR buffers contain dithiothreitol, which destabilises the thiol bond between the gold nanoparticles and the primers and which can—especially under thermal strain, e.g., during denaturation—lead to primers detaching themselves from the nanoparticles. Covalent bonds with more than one thiol between the primers and the nanoparticles can decrease the detachment of the primers and thus improve PCR efficiency.

In a preferred embodiment, countersequences are used, which can bind to such oligonucleotides, which have detached themselves from nanoparticles with which they had been connected previously. Countersequences are oligonucleotides. In the method, it can occur that oligonucleotides, which are conjugated to nanoparticles, detach themselves from said nanoparticles and become free. In the case that said free oligonucleotides are the primers according to the invention, these free primers can bind to the original or the complement. As the free primers are not bound to the nanoparticles, the free primers cannot be dehybridised from the original or complement, respectively, by excitation of the nanoparticles. Thereby, the efficiency and sensitivity of the method is decreased. The countersequences are at least partly complementary to the free oligonucleotides and bind to these with sufficient affinity to limit the function of the free oligonucleotides. In this way, the efficiency and sensitivity of the method can be increased. In a particularly preferred embodiment of the method, an amount of countersequences sufficient to block free primers is added to the sample even before the addition of the original. At the same time, said amount is small enough for the nanoparticles to display a sufficiently large number of non-blocked primers. This is possible if the number of primers on the nanoparticles exceeds the number of free primers.

In a preferred embodiment, filling molecules are attached to the nanoparticles. The filling molecules prevent the undesired aggregation of the nanoparticles in the sample. Thus, the filling molecules advantageously serve to stabilise the nanoparticles. The charge of the nanoparticles can be modulated using the filling molecules. In this way, the salt concentration, which is present in the environment of the nanoparticles, can be adapted such that the DNA polymerase can synthesise as quickly as possible and that, advantageously, the method can be performed rapidly. The filling molecules can consist of oligonucleotides that are not primers and which are preferably shorter than the primers. The filling molecules can also, e.g., consist of polymers, such as, e.g., polyethylene glycol. In a preferred embodiment, the filling molecules permit to decrease the number of primers on the nanoparticles and to instead use more filling sequences without decreasing the efficiency of the method by a significant amount.

In a further preferred embodiment of the method, the oligonucleotides on the nanoparticles show a spacer sequence as a partial sequence. The spacer sequence is situated in the part of the oligonucleotide closer to the nanoparticle. In this way, the spacer sequence serves the remaining part of the oligonucleotide as a spacer. In a preferred embodiment, an oligonucleotide contains one partial sequence, which has the function of a primer and is termed a primer sequence, as well as a partial sequence, which is a spacer sequence. As the primer sequences are spaced further away due to the spacer sequences, the nucleic acids to be amplified and the DNA polymerases can, advantageously, attain a better access to the primer sequences. In a preferred embodiment, the copies of the original and of the complement remain attached to the surface of the nanoparticles via the spacer sequences. In a particularly preferred embodiment, the spacer sequences contain restriction sites for restriction endonucleases such that the synthesised copies can be cut off the nanoparticles.

This preferably takes place after the termination of the method; however, it can also occur while the method is being carried out. That way, the method makes it possible to produce copies of nucleic acids, which are freely present in the sample. In a preferred embodiment of the method, the spacer sequences are at least as long as the filling molecules such that the primer sequences are not obscured by the filling molecules.

In a preferred embodiment, the heat, which is transferred from the nanoparticles to their environment through excitation of the nanoparticles, is sufficient to dehybridise the oligonucleotides on the surface of the nanoparticles from nucleic acids hybridised to said oligonucleotides. In this embodiment, the nanoparticles are conjugated to oligonucleotides and at least a part of the said oligonucleotides is hybridised to at least partially complementary nucleic acids. Through the excitation of the nanoparticles, thermal energy is transferred to the surrounding water, such that, preferably, the temperature of the water around the nanoparticles is sufficient, dehybridise the oligonucleotides from the nucleic acids bound thereto. In a particularly preferred embodiment, the method according to the invention is a PCR and the nanoparticles are conjugated with primers. When carrying out the PCR, preferably double stranded PCR products are formed, in each of which at least one single strand of the double stranded PCR products is conjugated to a nanoparticle. In this embodiment it is advantageously achievable to produce the denaturation temperature around the nanoparticles through the excitation of the nanoparticles and to carry out the denaturation of the double-stranded PCR products, without heating the entire reaction volume. In this way, the denaturation can be accelerated, such that the PCR can occur more rapidly. In another preferred embodiment, the annealing temperature and the elongation temperature are also produced through the excitation of the nanoparticles. In this way, preferably, only a small amount of energy has to be transferred when compared with the heating of the entire probe to the annealing temperature and elongation temperature. More preferably, denaturation, annealing and elongation of the PCR takes place without a global heating, but exclusively through local heating by excitation of the nanoparticles. That way, the method can be carried out without a device for global heating, such that less equipment is required to perform the method.

In another preferred embodiment, the method comprises a global heating step. In this, the temperature in at least one step of the method is reached at least partially by global heating. In a more preferably embodiment of the invention, the method is a PCR and the annealing temperature is attained by global heating of the reaction volume. Most preferably, the reaction volume is heated globally throughout the entire method to within a predetermined temperature range, in which annealing takes place. In this, the elongation temperature and denaturation temperature are reached through excitation of the nanoparticles. Thereby, advantageously, the device, which produces the global heating, can be implemented in a simple design as it only needs to sustain a predetermined temperature.

In another preferred embodiment, the annealing temperature and the elongation temperature are reached by global heating, exclusively the denaturation is achieved by the excitation of the nanoparticles. In this way, advantageously, it can be accomplished that the device that creates the global heating, needs to only produce a temperature cycle with two different temperatures and can thus be implemented in a simple design. Typically, the elongation and the annealing take place in a narrow temperature range. As opposed to this, to achieve denaturation, a certain temperature has to be surpassed only. Thus, inhomogeneities in the excitation of the nanoparticles to produce denaturation are a lesser problem than in the adjustment of the annealing temperature and elongation temperature. Hence, a preferred embodiment, in which the excitation of the nanoparticles exclusively serves to produce denaturation, can be technically implemented in a simpler fashion. This is particularly true for the preferred case, in which annealing temperature and elongation temperature are very close to each other, e.g. when the annealing temperature is 60° C. and the elongation temperature is 72° C., such that the global heating only needs to produce a small temperature increase.

In an especially preferable embodiment, the annealing temperature is the same as the elongation temperature. In this case, the method is a PCR. If the annealing temperature is equal to the elongation temperature, a temperature cycle with only two different temperatures is necessary to carry out the PCR, which means that the method can be performed with a simple setup.

Preferably, the melting temperatures of the primers and the DNA polymerase used are chosen such that at the melting temperature, the DNA polymerase used can still synthesise DNA at a sufficient speed. In an especially preferred embodiment, the elongation temperature, which is equal to the annealing temperature, is achieved by global heating and the denaturation is attained through the excitation of the nanoparticles. In this way, the device that produces the global heating can be implemented in a simple manner as it only needs to keep one temperature.

In a preferred embodiment, only a part of the nanoparticles are excited at any one point during the execution of the method. To this end, e.g., the means for the excitation of the nanoparticles can be designed in such a way that they only excite the nanoparticles in one part of the reaction volume. In an especially preferred embodiment, the nanoparticles are excited optically using a laser and the optics, which guide the light into the reaction volume is designed such that light is only directed into one part of the reaction volume. The part of the nanoparticles, which is excited, preferably changes during the execution of the method. In other words, a first set of nanoparticles, which is excited at a first time is not identical with a second set of nanoparticles excited at a second time. In this case, any number of nanoparticles can be present in the first and any number of nanoparticles can be present in the second set as long as the first and the second set are not identical. Of the two said sets one, e.g., can overlap with the other, such that the sets form an intersection of the sets. One set can, e.g., be a subset of the other set, such that the one set contains fewer nanoparticles than the other set. The two sets can also be modelled in a way that they do not form an intersection, such that no nanoparticle is present in the first set as well as the second set. One of the two sets can also be the empty set such that, e.g., at one time the nanoparticles are excited and at another time, no nanoparticles are excited. In a preferred embodiment, the first and the second set essentially contain the same number of nanoparticles. Especially preferably, at different times, a laser excites different fractions of the nanoparticles. Thereby, in the execution of the method, a laser with a lower power can be employed, which is only just sufficient, to excite a fraction of the nanoparticles. In an especially preferred embodiment, two or more lasers are used to excite different parts of the nanoparticles. This way, advantageously, it is possible to excite different fractions of the nanoparticles, without requiring an optical element, which directs the laser to different parts of the reaction volume.

In another preferred embodiment of the invention, a directed movement of the sample relative to an exciting field is taking place such that at different times, nanoparticles in different partial volumes of the sample are excited. More preferably, the exciting field is the light of a laser. In a most preferable embodiment, the light of the laser is directed by an optical element to excite nanoparticles in different partial volumes of the reaction volume at different times. The optical element can be moveable, e.g., the optical element can contain a movable mirror, a spatial modulator or an acousto-optical modulator. The laser itself can also be movable. The movement of the sample can be implemented by moving the reaction vessel, which contains the sample. In an especially preferred embodiment, the laser beam as well as the reaction vessel is moved. In a further preferred embodiment, the sample is moved in the reaction volume such that the light of the laser captures different partial volumes of the sample at different times. This can, e.g., be achieved by stirring the sample in the reaction volume, e.g., by using a magnetic stirrer. The reaction volume can, e.g., take an elongated shape, e.g., a channel or a tube. The sample can, e.g., be moved through a channel with the sample passing a laser beam in one or several places. Preferably, the sample flows through a channel and passes n positions, at each of which one laser beam is directed to the sample in the channel; due to the linear flow of the sample across the n laser beams, a PCR with n cycles is performed. In this way, the method can be carried out with small amount of movable parts. By using a channel, a miniaturisation, e.g., in the sense of a lab on a chip, is possible. Preferably, the laser beam causes the denaturation while elongation temperature and annealing temperature is produced by global heating. It is especially preferred that the elongation temperature is equal to the annealing temperature such that only one temperature has to be kept through global heating. In this way, the method according to the invention can be performed with minimal effort.

In a preferred embodiment, a thermolabile DNA polymerase is used in the method. For the case, in which the excitation of the nanoparticles is used for the denaturation, the exposure of the entire reaction volume to high temperatures can be avoided. Rather, it is possible to exclusively heat the immediate environment of the nanoparticles to the denaturation temperature. In this way, the DNA polymerases, which are not located in the immediate environment, are not exposed to high temperatures. Thereby, it is possible to use DNA polymerases, which are not thermostable, but thermolabile. By the inclusion of thermolabile DNA polymerases, a greater choice of polymerases is available for the method according to the invention. Due to the greater choice of DNA polymerases, the reaction conditions can be varied to a larger extent while at the same time maintaining sufficient operation of the DNA polymerase used. In order for the nucleic acids to be amplified to be able to bind to the negatively charged oligonucleotides on the nanoparticles, it may be necessary to use substances, particularly salts, in the sample at a concentration that can have a detrimental effect on the operation of a thermostable DNA polymerase, which decreases the efficiency of the method. The greater choice of DNA polymerases—in particular those with a high salt tolerance—can lead to an increase of efficiency of the method. Part of the greater choice of DNA polymerases are small DNA polymerases such as, e.g., the Klenow fragment and Phi29. In close proximity to the nanoparticles, large, thermostable DNA polymerases may experience steric hindrance due to the attached and possibly already elongated primers. As a result, it may be that the DNA polymerase does not arrive at the nucleic acid to be copied or the DNA polymerase is interrupted before it has synthesised a complete copy of the original or the complement, which causes in a decrease of the efficiency of the method. The greater choice of DNA polymerases, thus, makes an increase in the efficiency of the method possible. Due to the greater choice in DNA polymerases, advantageously, enzymes with lower production costs are available as well. The DNA polymerases that are not situated in the immediate environment of the nanoparticles, experience a smaller extent of heat induced deactivation. Thereby, advantageously, a smaller amount of DNA polymerase can be used in the method.

In a preferred embodiment of the invention, soluble primers as well as primers on nanoparticles are present in the reaction volume. The soluble primers are not conjugated to nanoparticles, but are dissolved in the sample. Preferably, the soluble primers are smaller than the nanoparticle primer conjugates and can, thus, exist in a larger concentration than the nanoparticle primer conjugates. Due to this, the soluble primers can have a better and faster access to long, double stranded nucleic acids, such as, e.g., genomic DNA. In an especially preferred embodiment, in a first step of the method, the long double stranded nucleic acids are denatured by global heating of the entire reaction volume, after which the soluble primers hybridise with the nucleic acids. The PCR, at first, runs through one or several cycles with global heating, during which the DNA polymerase synthesises the desired, short copies of the long double stranded nucleic acids. Subsequently, the PCR is continued, also using local heating through the excitation of the nanoparticles.

In a preferred embodiment of the invention, the particle diffusion of the nanoparticle primer conjugates can be amplified by using optical fields. Through optical vortex fields (in accordance with Silvia Albaladejo et al., Nano Letters, 2009, volume 9, issue 10, pages 3527 to 3531, the related content of which forms part of the present disclosure by way of reference), with which the nanoparticles are excited or due to optical forces (according to Arthur Ashkin et al., Proc. Natl. Acad. Sci., 1997, volume 94, issue 10, pages 4853 to 4860, the related content of which forms part of the present disclosure by way of reference), which are exerted onto the nanoparticles, the nanoparticle diffusion can be increased. Thereby, advantageously, a faster hybridisation of the nucleic acid to be amplified with the primers on the nanoparticles can take place at a given nanoparticle concentration. This can be utilised to achieve an acceleration of the method according to the invention.

In an embodiment of the invention, the concentration of the products of an amplification reaction can be detected with test probes. Test probes are nanoparticles, which contain oligonucleotides with test sequences on their surfaces. In a preferred embodiment of the method, the oligonucleotides of the test probes have a spacer sequence as a partial sequence. The spacer sequence is situated on the side of the oligonucleotide closer to the nanoparticle. Thus, the spacer sequence serves the remaining part of the oligonucleotide as a spacer. In a preferred embodiment, the oligonucleotide of the test probes contains both a partial sequence, which is termed a test sequence, and a partial sequence, which is a spacer sequence. In a preferred embodiment, the test probes have filling molecules attached thereto. The test sequences can hybridise with products of the amplification reaction. In this, the test sequences are preferably at least partially complementary to the products of the amplification reaction. In a preferred embodiment, first nanoparticles are conjugated to forward primers. In the presence of the original and a DNA polymerase, the forward primers are extended such that complements are created, which are bound to the first nanoparticles via the forward primers. In this, a complement consists of a forward primer and an extension sequence, which is created by the extension of the forward primer. Especially preferably, a PCR is performed using soluble and/or nanoparticle conjugated reverse primers such that in an exponential amplification, preferably a large number of copies of the original and of nanoparticle conjugated complements are produced. Most preferably, the first nanoparticles contain on their surface both forward and reverse primers. In an optional intermediate step, the originals and, possibly, their copies are denatured from the complements through local or global heating. The first nanoparticles are then brought together with the test probes, if this has not taken place before. The test sequences of the test probes are complementary to the extension sequences such that the test probes can bind to the extended forward primers on the first nanoparticles via the test sequences. In appropriate reaction conditions, the connection of the first nanoparticles and the test probes takes place to the extent, in which the nanoparticle bound complements are present. This means that if no extension sequences are formed, no connection between test probes and nanoparticles is made. More preferably, the reaction conditions of the amplification and the detection according to the invention using test probes are chosen such that the extent of the connection of the first nanoparticles with the test probes allows for a conclusion to be drawn as to what concentration of the original was present in the sample before the amplification. Through the connection of the first nanoparticles to the test probes, a measurable change can arise, e.g., a red shift or broadening of the plasmon resonance in the absorbance spectrum. In an especially preferred embodiment, the measurable change, which occurs through the connection of the test probes with the nanoparticles, is proportional to the concentration of the original in the sample before the amplification. In this way, advantageously, simple tools can be used to verify the concentration.

In another preferred embodiment, the method comprises forward primers, which are conjugated to first nanoparticles and free and/or nanoparticle bound reverse primers. It is especially preferred for the nanoparticles to contain forward as well as reverse primers on their surface. In a first step, a DNA polymerase extends the forward primers to nanoparticle bound complements in the presence of the original. In a second step, starting from the reverse primers, which bind to the nanoparticle bound complement, copies of the original are synthesised. After that, the first nanoparticles are brought together with the test probes, if this has not already occurred. In this embodiment, the test sequences are complementary to the forward primers. If the forward primers were not extended then the test probes can bind well to the first nanoparticles. If the forward primers were extended then the binding of test sequences to the forward primers is inhibited due to steric hindrance. If a newly synthesised copy of the original is hybridised with an extended forward primer then the binding of the test sequence to the extended forward primer is prevented. In this way, the extent of the connection between the first nanoparticles and the test probes decreases to the extent, in which the products of the amplification reaction, i.e., complements and copies of the original, are synthesised. When choosing the reaction conditions appropriately, the concentration of the original can be detected such that a measurable change is the smaller the more original was present in the sample before the amplification. The measurable change can, e.g., be a red shift or a broadening of the plasmon resonance in the absorbance spectrum. In this way, advantageously, a simple test can be designed, which allows for the determination of concentrations of specific nucleic acids.

The invention makes it possible to provide an improved method for the amplification of nucleic acids.

DETAILED DESCRIPTION OF THE INVENTION ACCORDING TO SEVERAL EMBODIMENTS

Figure 1:
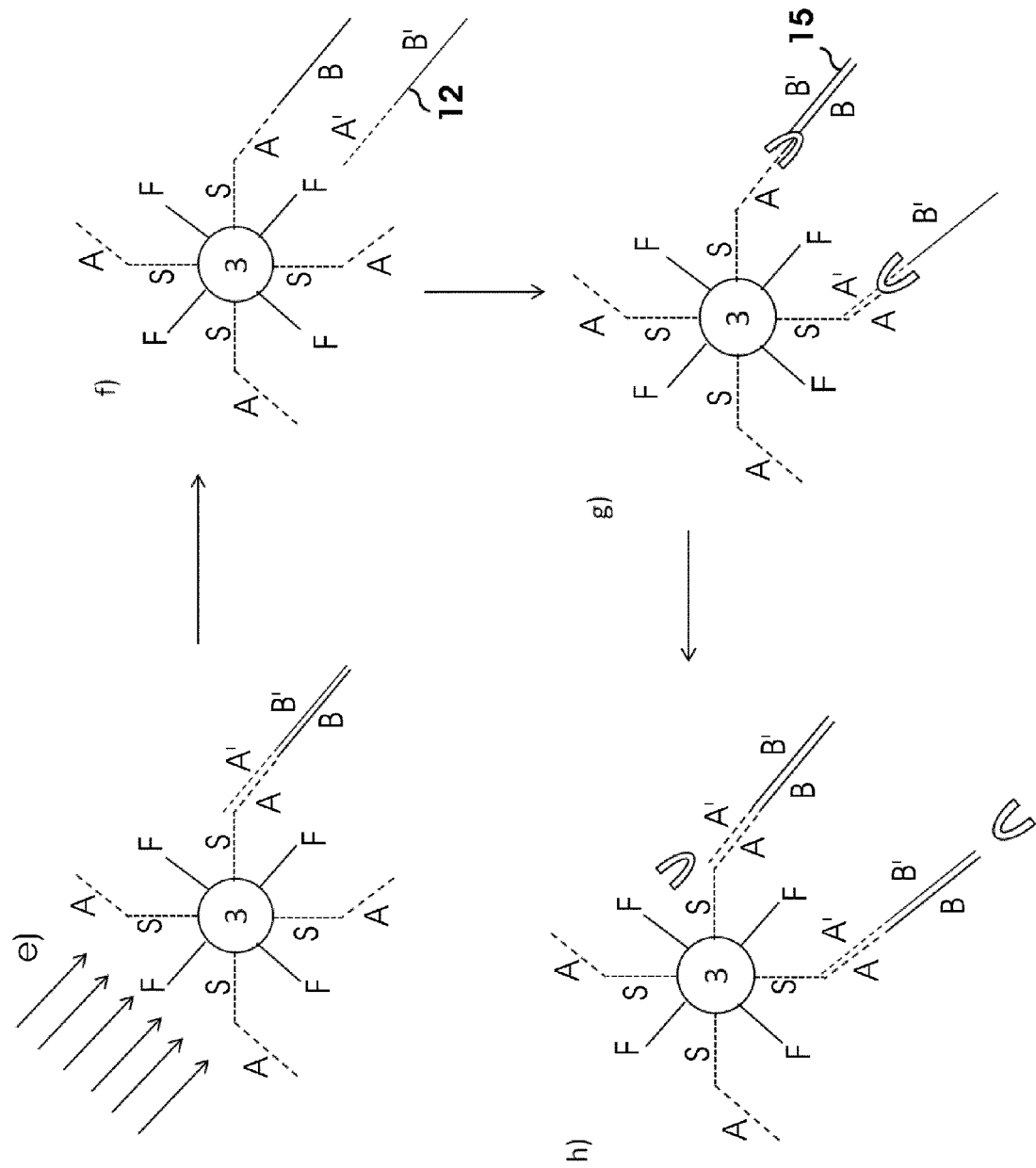
FIG. 1 shows in a schematic representation, the nanoparticles according to the invention conjugated to filling molecules, spacer sequences and primer sequences.

FIG. 1 shows an embodiment of the method according to the invention for the amplification of nucleic acids 1, which is implemented as PCR. A reaction volume 2 contains first nanoparticles 3. The first nanoparticles 3 show oligonucleotides 4 on their surface as seen in FIG. 1a. One kind of oligonucleotides 4 each contain as a partial sequence a primer sequence 5 with a sequence A and as an additional, optional partial sequence a spacer sequence 6 S. A primer sequence 5 is defined as the sequence of a primer 7. The spacer sequence 6S serves to keep the primer sequence 5 far enough away from the surface of the nanoparticle 8 for a nucleic acid 1 to be amplified to bind to the primer sequence 5 with a better efficiency and for the DNA polymerase 10 to find better access to the primer sequence 5. The oligonucleotides 4 with a primer sequence 5 A are attached, e.g., via a thiol bond to the surface of the first nanoparticle such that the 3'-end is facing away from the first nanoparticle 3. Optionally, another kind of oligonucleotides 4 can be present on the surface of the first nanoparticles 3; these are the filling molecules 9 F. Using the filling molecules 9, the charge of the nanoparticles 8 can be modulated such that undesired aggregations of the nanoparticles 8 are avoided. Furthermore the filling molecules 9 can increase the distance of the primer sequences 5 to each other on the surface of the nanoparticles 8 such that the nucleic acids 1 to be amplified and the DNA polymerase 10 can find a better access to the primer sequences 5. This can increase the efficiency of the method. The spacer sequence 6 is preferably at least as long as the filling molecule 9 such that, advantageously, the primer sequences 5 protrude from the filling molecules 9.

A sample 11 is present in the reaction volume 2, which sample 11 contains the first nanoparticles 3 from FIG. 1a with the primer sequences 5, spacer sequences 6 and filling molecules 9 and, in addition to this, the dNTPs and DNA polymerases 10. A nucleic acid 1 to be detected can be present in the sample 11. In this embodiment, the nucleic acid 1 to be detected is a DNA single strand, which is also termed the original 12 and contains a partial sequence A' as well as a partial sequence B'. The original 12 can contain further partial sequences, e.g. as overhang on the 5' or 3'-end or between the two partial sequences A' and B'. In FIG. 1 b, the original 12 binds with its partial sequence A' to the primer sequence 5 A on the surface of the first nanoparticle 3. In FIG. 1c, it is shown that a DNA polymerase 10 binds to the original 12 and to the primer sequence 5 A hybridised to the original 12. Subsequently, the DNA polymerase 10 synthesises in an elongation step, which is shown in FIG. 1d, starting from the 3' end of the primer sequence 5 A a nucleic acid 1 complementary to the original 12, which nucleic acid is termed the complement 13 and is connected to a spacer sequence 6 on the surface of the first nanoparticle 3. In FIG. 1e, the first nanoparticle 3 is then irradiated with light, which is absorbed by the first nanoparticle 3 on account of its plasmonic or material properties and which is transformed into heat. The heat is transferred to the environment of the first nanoparticle 3 and within the region of the original 12 and the newly synthesised complement 13 hybridised to the original 12 is sufficient for the original 12 to denature from the complement 13. The original 12 is now free again, as shown in FIG. 1f such that it can bind to another primer sequence 5 and further nanoparticle bound complements 13 can be synthesised in additional cycles of the method. In this way, a linear increase of the concentration of the complements 13 is created with an increasing number of cycles. The steps of the method described in FIGS. 1g and 1h are clarified in this document further below.

Figure 2:
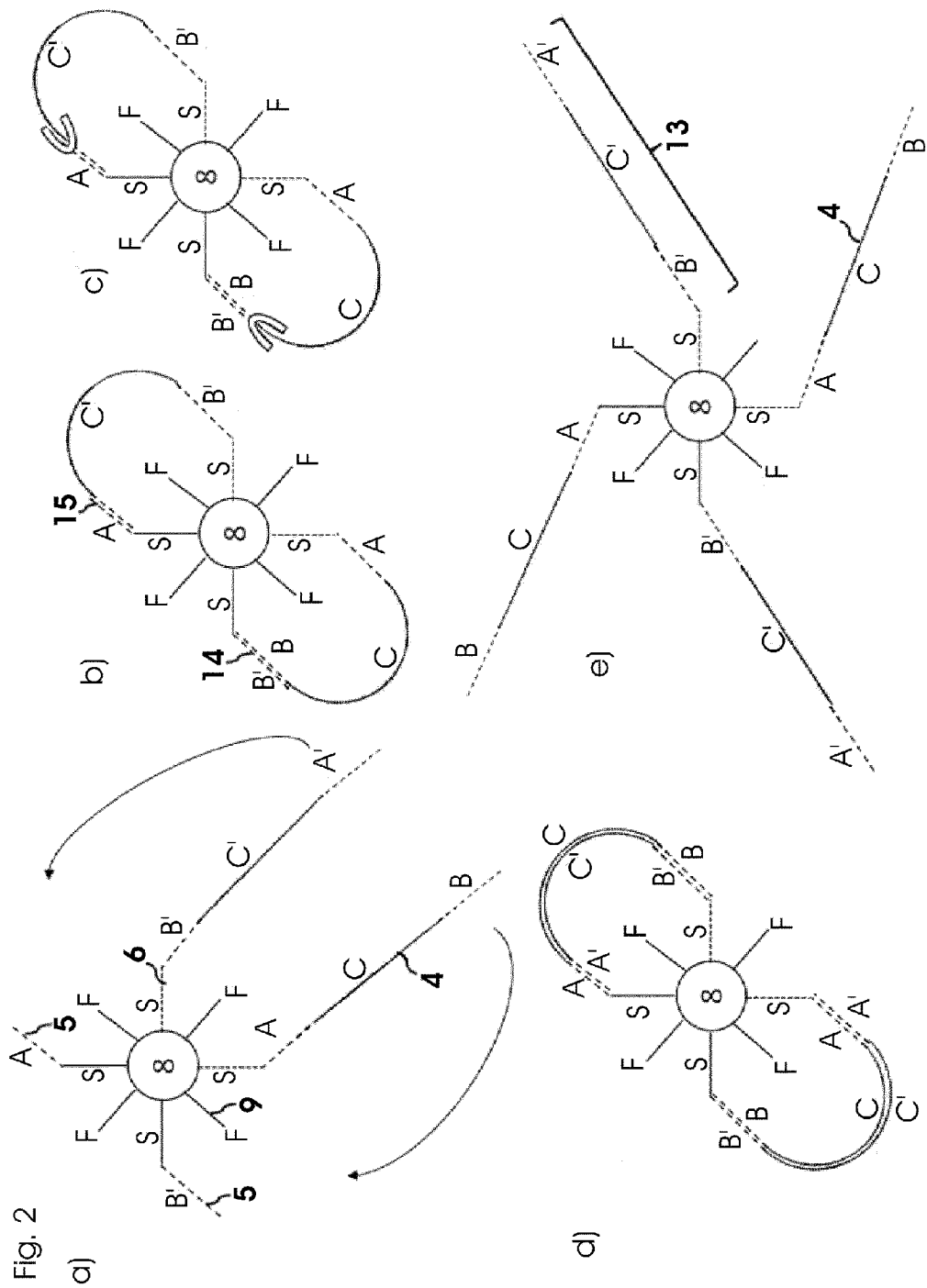
FIG. 2 shows in another schematic representation, the nanoparticles according to the invention conjugated to filling molecules spacer sequences and primer sequences.

FIG. 2 shows an embodiment of the method according to the invention, in which the nanoparticles 8 are situated in a sample 11. The nanoparticles 8 show filling molecules 9 F on their surface. Furthermore, the nanoparticles 8 are conjugated to oligonucleotides 4. A first kind of oligonucleotides 4 consists of a spacer sequence 6 S and a primer sequence 5 A. A second kind of oligonucleotides 4 consists of a spacer sequence 6 S and a primer sequence 5B'. In this embodiment, the original 12 to be amplified is a single stranded DNA molecule with the partial sequences A, C, B (not shown). Starting from a primer sequence B' on the surface of the nanoparticle 8, a DNA polymerase 10 synthesises a strand complementary to the original 12 such that, as shown in FIG. 2a, a DNA single strand with the sequence S, B', C', and A' is situated on the nanoparticle 8. At the same time, it can be seen on FIG. 2a that a DNA polymerase has synthesised a copy of the original 12 starting from the primer sequence 5 A, which is connected with the spacer sequence 6 S on the surface of the nanoparticle 8. As shown by the arrow in FIG. 2a, the copy of the original 12 attached to the nanoparticle 8 hybridises with its partial sequence B to a primer sequence 5 B' on the surface of the same nanoparticle 8. A second arrow in FIG. 2a shows that the complement 13 synthesised on the surface of the nanoparticle 8 hybridises with its partial sequence A' to a primer sequence 5 A on the surface of the same nanoparticle 8. The result of the two said hybridisations is shown in FIG. 2b. In this, the original 12 as well as the complement 13 form a loop on the surface of the nanoparticle 8. FIG. 2c shows that a strand complementary to the original 12 is synthesised starting from the primer 7 B', which strand is connected to the surface of the nanoparticle 8 via a spacer sequence 6 S. Another DNA polymerase 10 synthesises a copy of the original 12 starting from the primer sequence 5A, which copy is also connected to the surface of the nanoparticle 8 via a spacer sequence 6. The result of the two syntheses is shown in FIG. 2d. In this embodiment, the forward primer 14 as well as the reverse primer 15 are situated on the same nanoparticle 8. In this way, a newly synthesised DNA strand can hybridise back to a primer 7 on the same nanoparticle 8. This can lead to the acceleration of the method according to the invention as the newly synthesised DNA strand does not have to travel far to meet a complementary primer 7. Rather, the newly synthesised DNA strand can bind particularly rapidly to a complementary primer 7 on the surface of the same nanoparticle 8, which is facilitated especially by the high local concentration of the primer 7 on the nanoparticle 8. After the excitation of the nanoparticle 8 in FIG. 2d, e.g., with a laser 16, the copies of the original 12 and the copies of the complement, which are each attached to the surface of the nanoparticle 8 via spacer sequences 6, dehybridise. After that, a copy of the original 12, which is attached to the nanoparticle 8, can hybridise with a complement 13, which is attached to the surface of another, identical nanoparticle 8. Through the hybridisation, the nanoparticles 8 are connected, such that a measurable change occurs. The measurable change can, e.g., consist in a colour change of the sample 11. The embodiment of the method according to the invention shown in FIGS. 2a to 2e makes it possible to provide a simple test, which serves to detect the original 12.

Figure 3:
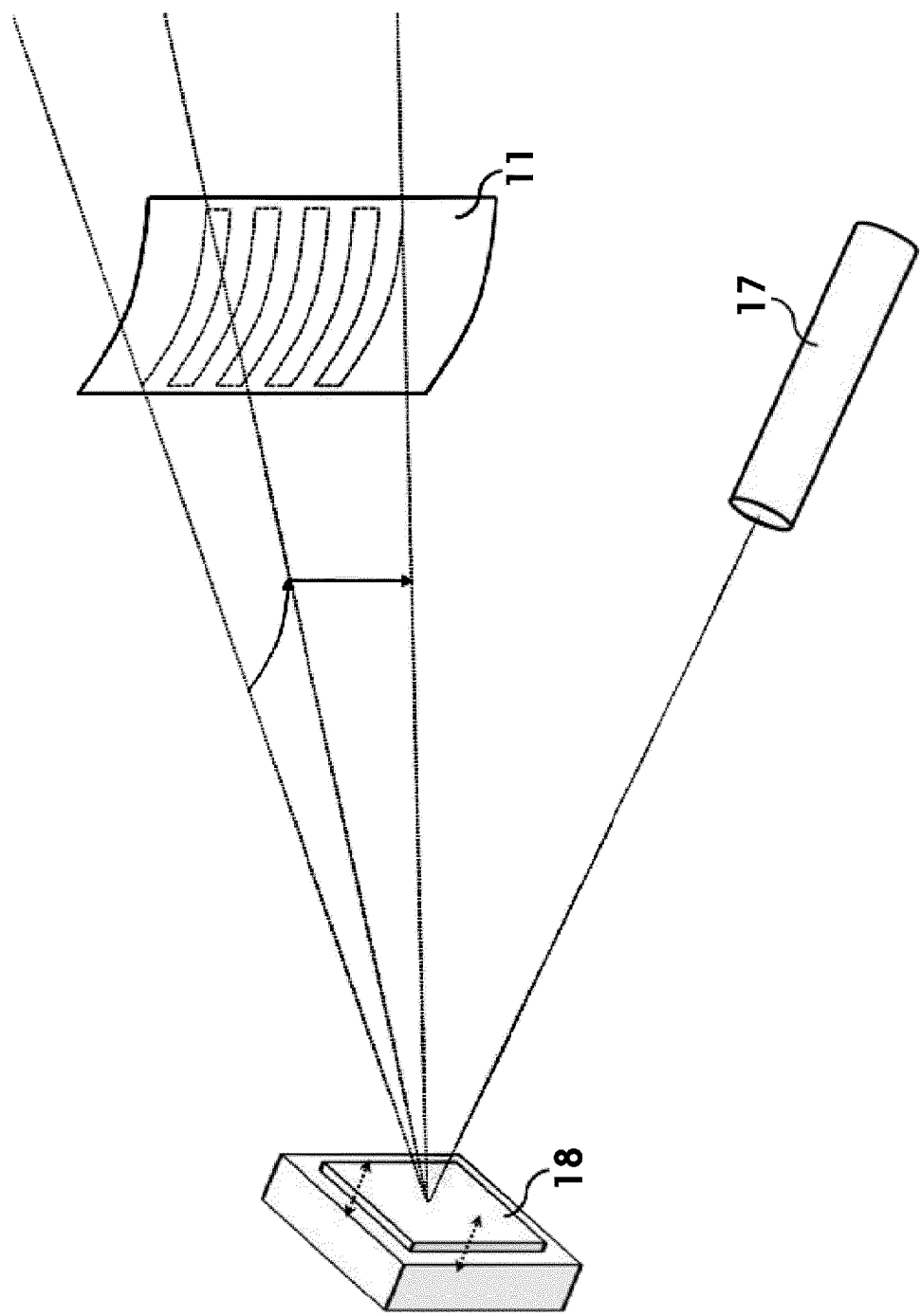
FIG. 3 shows in a schematic representation the setup for performing the method according to the invention with a laser, a two dimensional mirror scanner and a sample.

FIG. 3 shows a setup, which is suitable for carrying out the method according to the invention. The setup contains a light source 17, which in this case is implemented as a laser 16, and a two dimensional mirror scanner 18, which can direct light from the laser 16 to the sample 11. The two dimensional mirror scanner 18 can deflect the laser in two dimensions. In this setup, the denaturation in the sample 11 occurs by focussing a laser beam onto a part of the sample 11. During the method, the laser beam is deflected such that it hits different parts of the sample 11. In the example shown in FIG. 3, the laser beam is deflected by the mirror scanner 18 such that the laser beam moves through the reaction volume 2, in which the sample 11 is situated, row by row. In FIG. 3, the path followed by the laser beam in the sample 11 is shown in a dashed line. Due to the fact that at any one time during the method, only parts of the sample 11 are excited, lasers 16 with a smaller power output can be used. As excitations of under one microseconds are sufficient to denature DNA with the aid of optothermally heated nanoparticles 8, a typical focus diameter of a laser 16 of approximately 10 to 100 µm allows a laser beam to scan the sample 11 at a speed of approximately 10 to 100 m/s while leading to a denaturation of the DNA at each point that the laser sweeps across. This enables a very fast scanning of large sample volumes. The complete scanning of an area of 1 $cm^2$ takes, e.g., only 128 ms at a focus diameter of 78 µm and 128 rows at an inter-row distance of 78 µm and a row length of one centimeter at a velocity of the scanning laser beam of 10 m/s. Advantageously, this is significantly shorter than a denaturation step using global heating would generally require. Optical elements such as, e.g., a mirror scanner 18 shown in FIG. 3 and so called F-theta-lenses can achieve a good homogeneity of the focus quality and size across the entire sample 11 scanned. As an alternative to a continuously emitting laser 16, a pulse laser 16 or a thermic radiator can be used.

Figure 4:
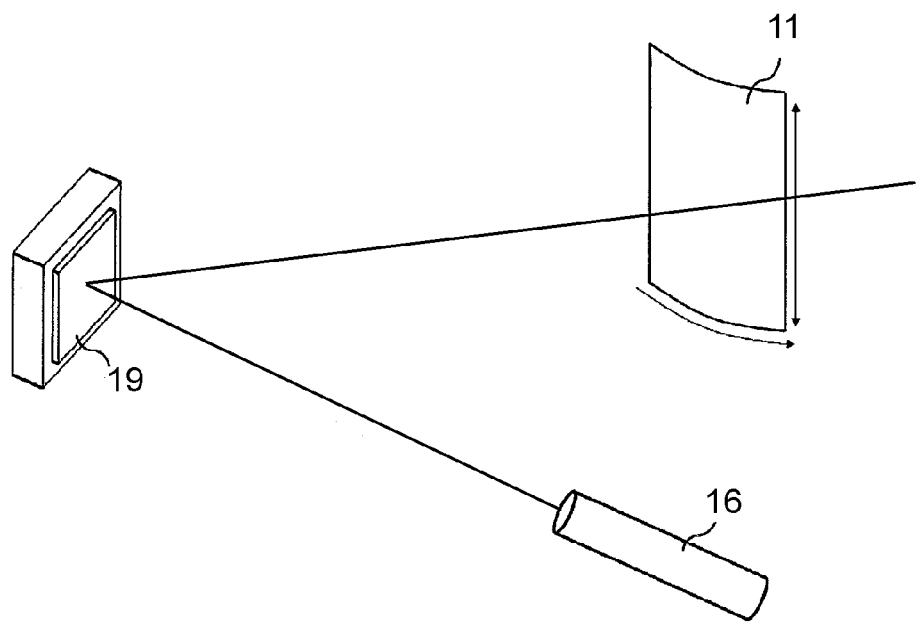
FIG. 4 shows in a schematic representation a further setup for carrying out the method according to the invention with a laser, a mirror, and a sample, which is moved relative to the laser beam.

FIG. 4 shows a setup for carrying out the method according to the invention in which a laser 16 and a mirror 19 are fixed and the laser beam of the laser 16 is directed towards the sample 11 using the mirror 19. In this, the sample 11 is arranged to be movable in two dimensions such that by moving the sample 11 the entire sample 11 or large parts of the sample 11 can be reached by the focus of the laser 16.

Figure 5:
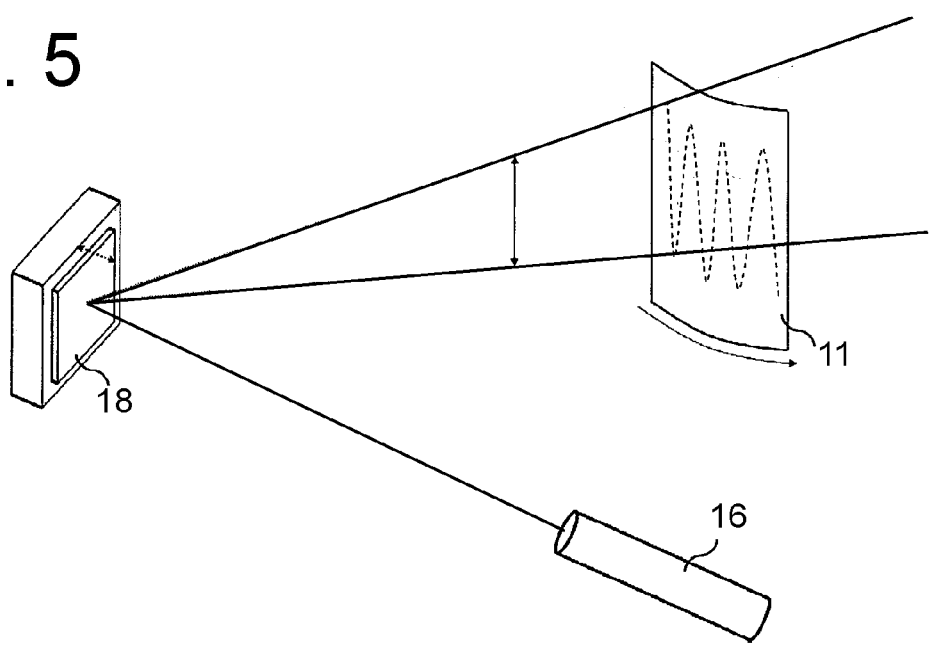
FIG. 5 shows in a schematic representation another setup for carrying out the method according to the invention with a laser, a one dimensional mirror scanner and a sample moved in one dimension.
Figure 6:
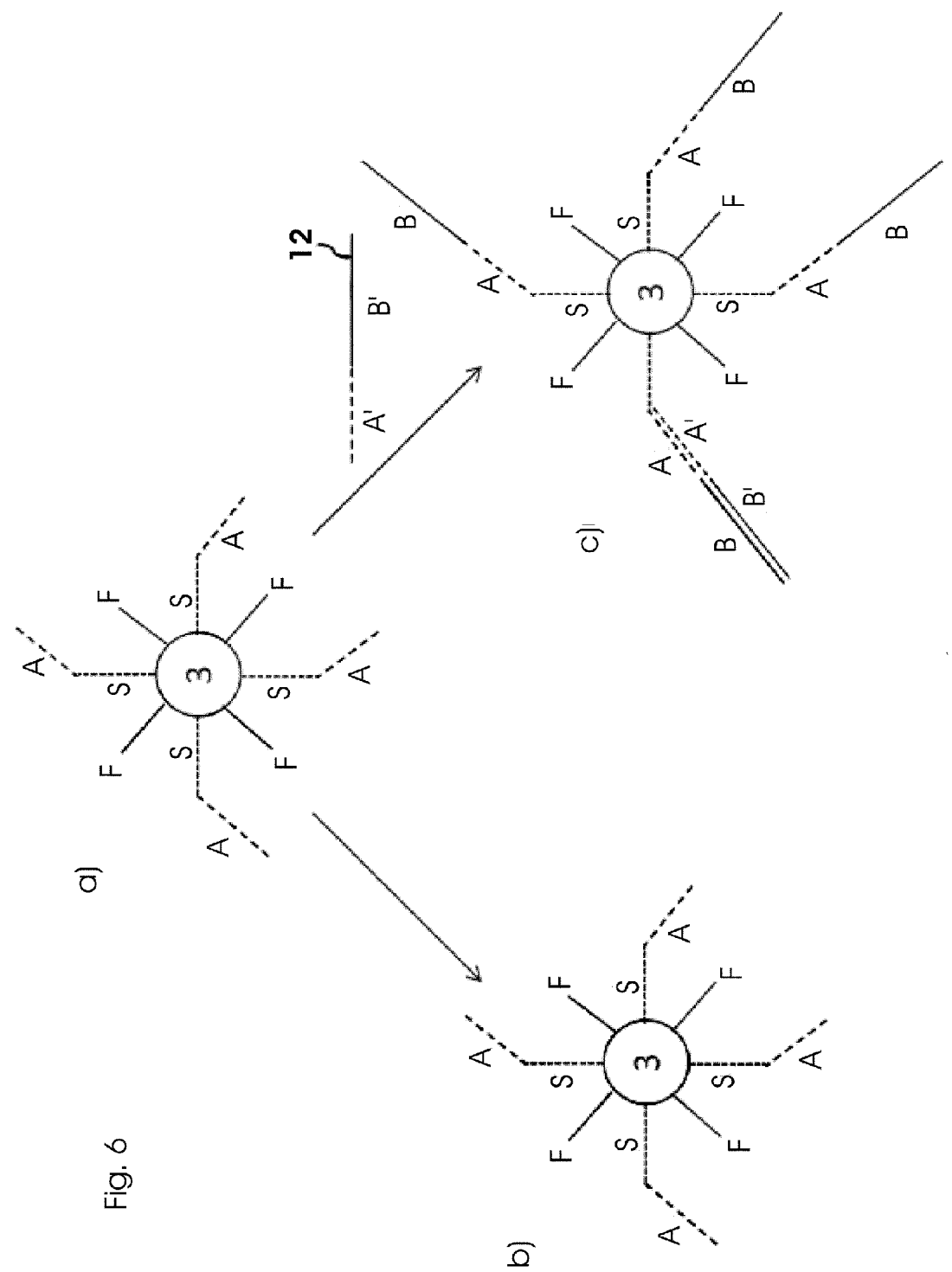
FIG. 6 shows in a schematic representation the nanoparticles according to the invention and the test probes according to the invention for the positive detection of DNA.

FIG. 5 shows a setup for carrying out the method according to the invention, in which a laser 16 is fixed, and a mirror scanner 18 can deflect the laser beam of the laser 16 in one direction. The sample 11 is arranged to be movable in one direction such that by moving the mirror scanner 18 and the sample 11 the entire sample 11 or large parts of the sample 11 can be reached by the laser beam. One possibility for detecting a nucleic acid 1 by PCR according to the invention is shown in FIG. 6. In this, first nanoparticles 3, which show filling molecules 9 F and first oligonucleotides 20 on their surface, are situated in a sample. The first oligonucleotides 20 consist of a spacer sequence 6 S and a primer sequence 5 A, as shown in FIG. 6a. If an original 12 with the partial sequences A' and B' is present in the sample 11 then the original 12 hybridises to the complementary primer sequence 5 A on one of the first nanoparticles 3. A DNA polymerase 10 synthesises the complement 13 with the partial sequences A and B, starting from the primer sequence 5 A such that the complement 13 is connected to the surface of the first nanoparticle 3 via the spacer sequence 6 S, as shown in FIG. 6c. In a next step, the test probes 21 shown in FIG. 6d are added to the sample. The test probes 21 are second nanoparticles 22, which shown filling molecules 9 and second oligonucleotides 23 on their surface. The second oligonucleotides 23 contain a spacer sequence 6 S and a test sequence 5 B'. The test sequence 5 B' can hybridise with the complementary partial sequence B of the complement 13 on the surface of the first nanoparticle 3, as shown in FIG. 6f. Thereby, the first nanoparticles 3 and the second nanoparticles 22 are connected such that a measurable change can occur. If the original 12 is not present in the sample 11, then no complement 13 is created on the surface of the first nanoparticle 3, as seen in FIG. 6b. As there is no complement 13 on the first nanoparticles 3, first nanoparticles 3 and second nanoparticles 22 cannot connect to each other and the measurable change does not occur. In this embodiment the sequence B' is complementary to the sequence B; the sequence B' can also be complementary to parts of the sequence A. The spacer sequence 6 S on the first nanoparticles 3 is identical to the spacer sequence 6 S on the second nanoparticles 22. In a further embodiment however, different spacer sequences 6 can be used on the first nanoparticles 3 and the second nanoparticles 22. Also, several different spacer sequences 6 can be used on the same kind of nanoparticles 8. The buffer and hybridisation conditions, e.g., temperature, salt concentrations, nanoparticle concentrations, concentrations of additional buffer additives, pH, are preferably chosen such that a hybridisation connecting the first nanoparticles 3 with the second nanoparticles 23 can only arise after the completed extension of the primer sequence 5 A on the first nanoparticles 3. The connection of the first nanoparticles 3 with the second nanoparticles 22 can, e.g., be detected as a red shift and broadening of the plasmon resonance in the absorbance spectrum. The connection can also be detected, e.g., by measuring the change in transmission at one or several wavelengths after optothermal excitation of the nanoparticles 8 and the resultant denaturation of the nucleic acids 1, which connect the first nanoparticles 3 with the second nanoparticles 22. The test probes 21 can be supplied in a special hybridisation buffer to which at least a part of the sample 11, which contains the first nanoparticles 3, is added after the step of the method, in which the synthesis of the complement 13 is enabled. The test probes 21 can, together with the first nanoparticles 3, be present in the sample already before the start of the method. In this case, the test probes 21 can be passivated such that they do not act as primer 7. The passivation of the test probes 21 can consist in choosing the primer sequence 5 on the test probes 21 in such way, that no hybridisation of the said primer sequence 5 with the original 12 occurs at the annealing temperature during the PCR, but only after subsequent lowering of the temperature. The passivation of the test probes 21 can be created by attaching the second oligonucleotide 23, which contain partial sequences of the original 12, at the 3'-end of the second nanoparticles 22 such that the DNA polymerase 10 cannot extend the second oligonucleotide 23. In this case, the second oligonucleotides 23 can be free on their 5'-end or connected to the second nanoparticles 22. The test probes 21 can also be passivated by a base modification, e.g., with dideoxy cytosine (ddC) at the free prime end of the second oligonucleotide 23, which prevents elongation.

Figure 7:
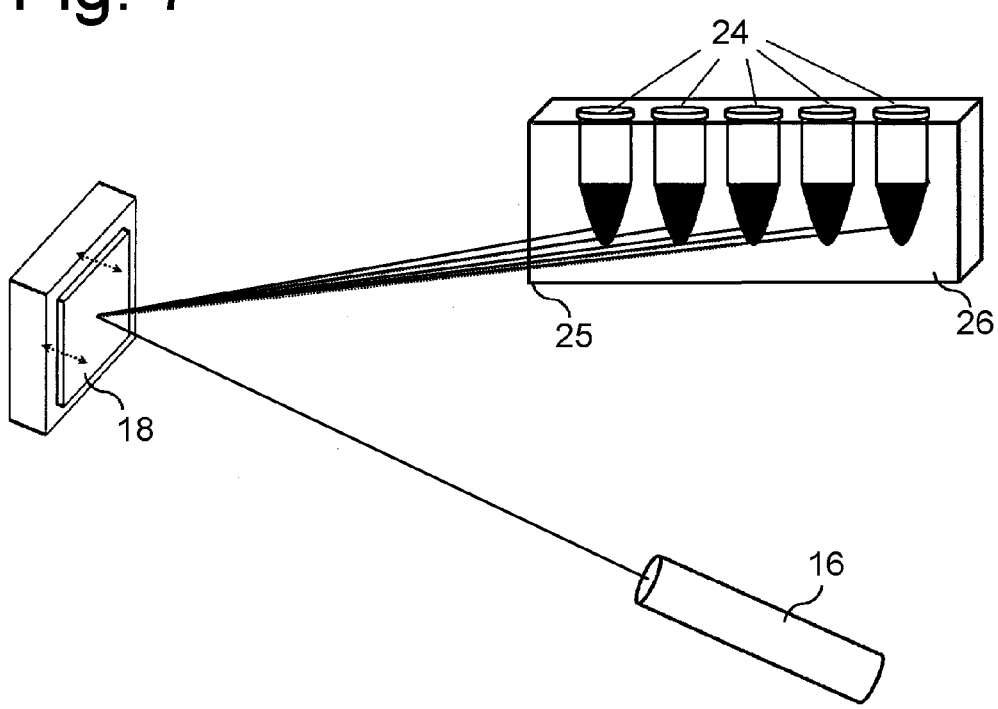
FIG. 7 shows in a schematic representation another setup for carrying out the method according to the invention with a laser, a two dimensional mirror scanner and a sample tube in a water bath.
Figure 16:
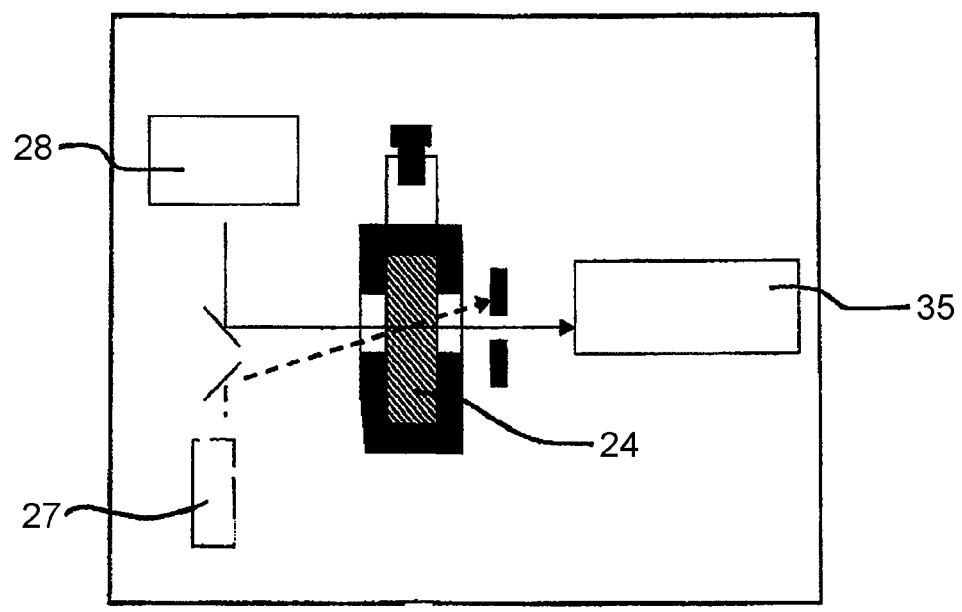
FIG. 16 shows in a schematic representation a first laser for the excitation of nanoparticles in a sample tube and a second laser and a photo diode for measuring the transmission of the sample.

In the embodiment of the method as shown in FIG. 6, first nanoparticles 3 made of gold and with a diameter of 60 nm are functionalised with oligonucleotides 4 (according to J. Hurst et al., Anal. Chem., 78(24), 8313-8318, 2006, the related content of which forms part of the present disclosure by way of reference). In this, one part oligonucleotide 4 ID1 and—as a filling molecule 9—four parts oligonucleotide 4 ID 2 are used. After functionalisation and six washing steps, the first nanoparticles 3 are present in a PBS buffer (20 mM PBS, 10 mM NaCl, 0.01% Tween 20, 0.01% azide, 1 mM EDTA, pH 7.5) at a concentration of 200 µl. The amplification reaction is performed in a total volume of 10 it in 200 it sample tubes 24 (5 it DreamTaq PCR Mastermix 2× (fermentas), 0.1 it NaCl 5 M, 0.1 it $MgCl_2$ 250 mM, 0.1 µl $MgSO_4$ 250 mM, 1 it of the functionalised first particles 200 µM, 1 it oligonucleotide 4 ID3 (as an original 12 to be amplified, wherein the concentration of the original 12 to be determined is in a total volume of 10 µl, e.g., 0 pM, 10 pM, 20 pM or 50 pM) dissolved in water with 100 nM oligonucleotide 4 ID4 (oligonucleotide 4 ID4 serves to saturate surfaces e.g., during the storage of the original 12 before the reaction), 2.7 it water). As shown in FIG. 7, the sample tubes 24 are brought to a temperature of 65° C. in a glass cuvette 25 in a water bath 26, wherein said temperature is the annealing as well as the elongation temperature. The water bath 26 serves—in addition to keeping the correct temperature—also the better coupling of the laser 16 into the non-planar surface of the sample tubes 24. The water in the water bath 26 enables the reduction of the difference in the refractive indices between the outside of the sample tubes 24 and its inside, which is filled with the PCR reaction mixture; thus a refraction of the laser beam and a resultant negative influence on focus quality and sharpness is suppressed. Thereby, advantageously, the coupling of the laser 16 is improved. The laser 16, which serves to excite the nanoparticles, is a frequency-doubled diode-pumped: Nd:YAg laser (Coherent Verdi V10) which is focussed into the sample tubes 24 in the water bath 26 (focal diameter approximately 20 µm) with an output power of 1.5 W with a F-theta-lens (Jenoptik, focal distance 100 mm) behind a mirror scanner 18 (Cambridge technologies, Pro Series 1). The mirror scanner 18 allows to move the focus row by row through the sample tubes 24, as already shown in FIG. 3, and thus to involve the entire PCR reaction volume in the optothermal amplification. Per sample tube 24, 400 rows are scanned with the focus at a distance of approximately 12 µm at a row speed in the sample tubes 24 of approximately 2 m/s. This corresponds to one cycle in the first sample tube 24. Subsequently, all the other sample tubes 24 are scanned one after the other, such that each sample tube 24 has experienced one cycle. After a waiting time of 40 s after the scanning of the first sample tube 24, the next cycle is started and this is repeated until each sample tube 24 has completed 25 cycles. As a starting concentration of the original 12 in the first sample tube 24, 0 pM, in the second sample tube 24 20 pM and in the third sample tube 24 50 pM is chosen. For the negative control, a fourth sample tube 24 is inserted into the water bath 26, which also contains the original 12 at a concentration of 50 pM, but is not hit by the laser beam. After the first, the second and third sample tubes 24 have completed 25 cycles, all four sample tubes 24 are removed from the water bath 26. To examine the effect of the laser cycles and the concentration of the original 12, a test probe 21 is used, which is able to exclusively hybridise to the test sequences produced through the extension of the nanoparticle bound primers under the chosen buffer and hybridisation conditions. In this, the extension of the primer 7 is complementary to the original 12, as shown in FIG. 6c. To produce the test probes 21, second nanoparticles 22 made of gold and with a diameter of 16 nm are functionalised with oligonucleotides 4 (according to J. Hurst, supra). Therein, one part oligonucleotide 4 ID5 and—as a filling molecule 9—four parts oligonucleotides 4 ID2 are used. After the functionalisation and six washing steps, the second nanoparticles 22 are present in a PBS buffer (20 mM PBS, 10 mM NaCl, 0.01% Tween 20, 0.01% azide, 1 mM EDTA, pH 7.5) at a concentration of 200 pM. For the hybridisation of the oligonucleotides 4 on the first nanoparticles 3 with the oligonucleotides 4 on the second nanoparticles 22, a modified phosphate buffer is used (13 mM PBS, 200 mM NaCl, 0.02% Tween 20, 1 mM EDTA, 20 mM sodium citrate, 1 µg/ml PVP10, pH 7.5). 10 µl hybridisation solution contain 2.25 µl of the modified phosphate buffer, 3 µl formamide, 2 µl NaCl 5M, 0.25 µl of the 200 pM test probe solution and 2.5 µl of the corresponding PCR solution from the optothermal amplification, which contains the first nanoparticles 3. If a sufficient amount of the original 12 with the sequence ID3 was present in the sample tube, the oligonucleotide 4 with the sequence ID1 on the surface of the first nanoparticle 3 is extended and is able to hybridise with the oligonucleotide 4 with the sequence ID5 on the surface of the test probe, as shown in FIG. 6f. The hybridisation is verified using optothermal excitation of the nanoparticles 8 (according to EP 2162549, the related content of which forms part of the present disclosure by way of reference). To this end, the sample tubes 24, as shown in FIG. 16, are hit with pulses from a first laser 27 (50 µs pulse duration, 532 nm wavelength, approximately 700 mW peak power, focus diameter approximately 30 µm). Thereby, the nanoparticles 8 are optothermally heated and transfer heat to their environment. If first nanoparticles 3 and second nanoparticles 22 are connected due to the hybridisation of oligonucleotides 4, as is shown in FIG. 6f, then they will be separated by the laser pulse. This can be detected using a second laser 28 (wavelength 630 nm, power 5 mW continuously) as shown in FIG. 16; the focus of the second laser (30 µM diameter) is superimposed with the focus of the first laser 27, which is preferably used for dehybridisation exclusively, the focus of the second laser detects the absorbance before and after the laser pulse of the first laser 27. The optical path on which the change in absorbance is induced optothermally and is measured amounts to approximately 2 mm. The intensity of the light of the second laser 28 transmitted through this layer is measured with a photo diode 35. The optothermally induced transmission change is determined from the difference of the current in the photo diode before and after the pulse, which transmission change is produced by the dehybridisation of the extended first oligonucleotides 20 and second oligonucleotides 23 between the nanoparticles 8 and the subsequent diffusion of the nanoparticles away from each other.

Figure 8:
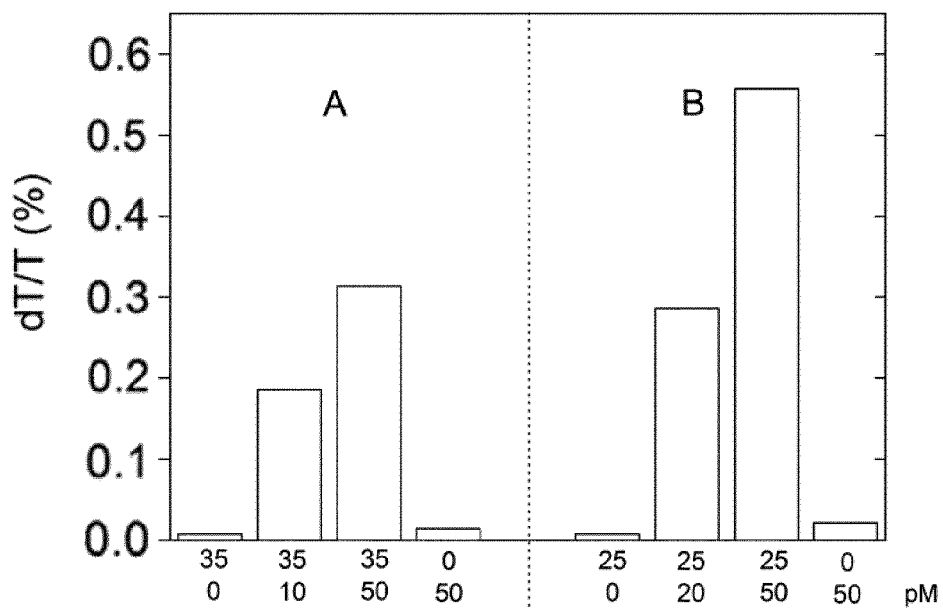
FIG. 8 shows in two diagrams the results of amplification reactions with global and local heating with test probes for the positive detection of DNA.
Figure 8:
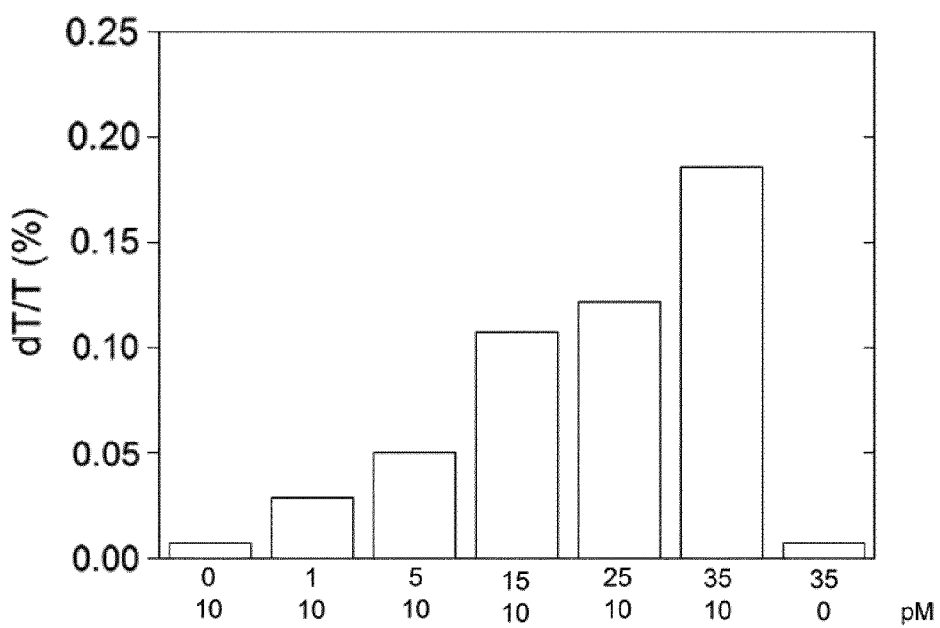

FIG. 8a shows the relative transmission change, which is produced by the laser pulse of the first laser 27 and the resultant dehybridisation of the oligonucleotides 4 between the first nanoparticles 3 and second nanoparticles 22; the relative transmission change is a measure for the presence of gold-DNA-gold-bonds in the sample tubes 24. Below the diagram in FIG. 8a, the number of completed cycles is shown in a first row. In a second row, which is situated underneath the first row, the concentration of the original 12 in the sample tube 24 before carrying out the amplification is shown in pM. On the right side of the diagram in FIG. 8a in the section B, the first, second and third sample tube 24 are shown from left to right, each of which has completed 25 optothermal cycles; in addition to this, the fourth sample tube 24, which has not received any optothermal treatment, is shown. It can clearly be seen that the measured transmission change as an indicator for the gold-DNA gold-bonds increases with the increasing concentration of the original 12 before the amplification when the 25 cycles have been completed. For the first sample tube 24 without original 12 and the fourth sample tube 24 without optothermal treatment, only a small transmission change is observed. This shows that, herein, no extension of the primer sequences 5 on the first nanoparticles 3 has taken place and thus, no binding to the test probe is possible. Only after completing the optothermal cycles and in the presence of the original, an extension of the primer sequences 5 on the first nanoparticles 3 can be created by the DNA polymerase 10, which leads to a connection of the first nanoparticles 3 with the second nanoparticles 22 and finally to a transmission change as a result of the optothermally induced separation of the nanoparticles 8.

As a comparison, FIG. 8a shows in section A on the left side the result of a corresponding experiment, which did not heat the DNA locally through optothermal excitation of the nanoparticles 8, but heated the entire reaction volume 2 globally in a conventional thermal cycler (Labnet Multi Gene II). From left to right, the first to fourth sample tubes 24 are shown, the content of which is identical to the one in the experiment described in the previous paragraph. First, second and third sample tubes 24 were subjected to a classical PCR protocol (93° C. for 1 s, 53° C. for 20 s, 35 cycles). As in the case of the optothermal heating, it can be observed that the more of the original 12 is present in each sample tube 24 before the amplification, the larger is the transmission change measured, which is created by the laser pulse and the resultant dehybridisation of DNA between the first nanoparticle 3 and the second nanoparticle 22 and which transmission change is the measure for the presence of gold-DNA-gold bonds in the solution. The fourth sample tube 24, while containing 50 pM of the original 12, has not been heated cyclically and shows almost no transmission change. In this case, the primer sequences 5 on the first nanoparticles 3 were not extended to a sufficient degree.

FIG. 8b shows a similar experiment with global heating of the entire reaction volume 2, however, the concentration of the original 12 in the sample tubes 24 is constant at 10 pM before the amplification (second row below the diagram), while the number of the cycles is increasing (first row below the diagram). Here, it can clearly be seen that with an increase in the number of cycles, the transmission change measured becomes larger, which is a clear sign that the more primer 7 on the first nanoparticles 3 are extended, the more cycles are completed and thus a clear sign that the origin of the signal measured is indeed the completed elongation of the oligonucleotides 4 on the first nanoparticles 3 by the DNA polymerase 10.

In an embodiment of the method, a free reverse primer 15, which binds to the 3'-end of the complement, is used after the elongation of the primer sequence 5 on the surface 4 of the first nanoparticles 3, during which extension a nanoparticle bound complement 13 is produced. FIG. 1g shows, that the complement 13 with the partial sequences A and B already synthesised, which is connected to the surface of the first nanoparticle 3 via a spacer sequence 6, hybridises with a primer 7 B', which was previously freely present in the sample 11. In this, the primer 7 has the sequence B' and is connected with the partial sequence B of the complement 13. Starting from the primer 7 with the sequence B', the DNA polymerase synthesises a copy of the original 12. In FIG. 1g it is also shown that the original 12 has bound to another primer sequence 5 A on the surface of the first nanoparticle 3 and a DNA polymerase 10 synthesises another complement starting from the primer sequence 5 A. The original 12, the copy of the original 12 and the two complements 13 connected with the first nanoparticle are shown in FIG. 1h. A subsequent denaturation through excitation of the first nanoparticles 3 results in the original 12 and its copy becoming free. In this, the original 12 as well as its copy can serve as a template for the amplification in subsequent steps of the method. After a waiting time, which might be necessary for the hybridisation of the original 12 and copies of the original 12 with the primer sequences 5 A on the first nanoparticles 3 and of free primers B' with the primer sequences 5 already elongated on the first nanoparticles 3, the next cycle of the method can be performed with another excitation of the first nanoparticles 3. Preferably, this cycle is repeated until a sufficient amount of extended primer sequences 5 are present on the first nanoparticles 3 and/or a sufficient amount of copies of the original 12 are present in the sample 11 to allow a verification of the amplification effected or, respectively, the presence of the original 12 in the sample 11. By using a free primer 7 B', as shown in FIGS. 1g and 1h, an exponential amplification of the original 12 is possible. In FIG. 1a to 1f, only a linear amplification of the nanoparticle bound complement 13 is achievable without this free primer 7. The denaturation of DNA can, in one embodiment, take place in less than one millisecond. Even at 40 cycles, the denaturation of the DNA and the subsequent cooling to the elongation temperature only require a few milliseconds in total in this embodiment. This means that the duration of the method according to the invention is not determined by technical limitations such as the heating and cooling rate of conventional thermocyclers. Also, the thermalisation times in the reaction volume 2 are avoided as the heat is always produced in the environment of the nanoparticles 8 and an equilibrium temperature distribution is effected within nanoseconds. Thereby, a PCR can be accelerated significantly.

Figure 9:
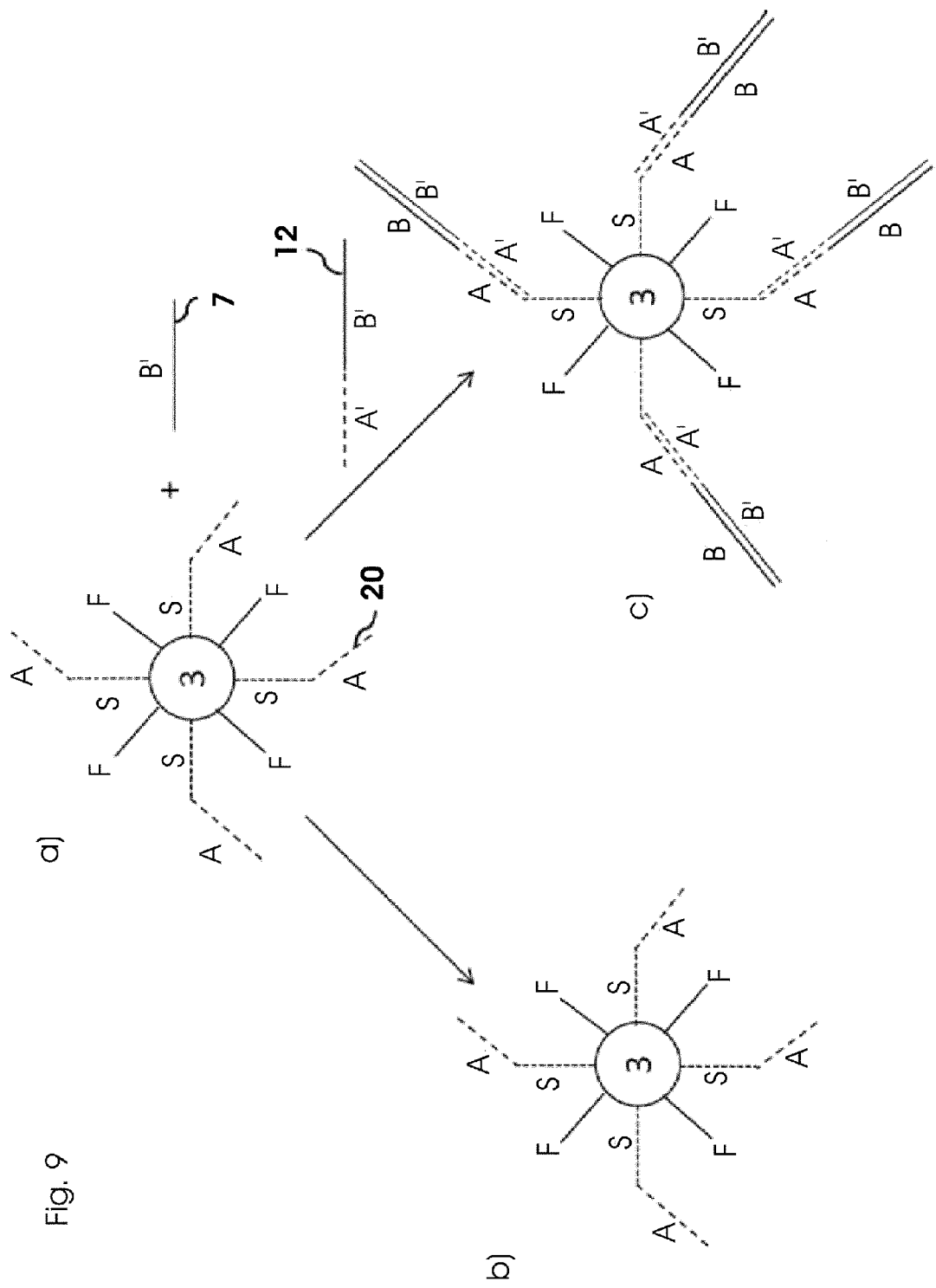
FIG. 9 shows in a schematic representation the nanoparticles according to the invention and the test probes according to the invention for the negative detection of DNA.
Figure 9:
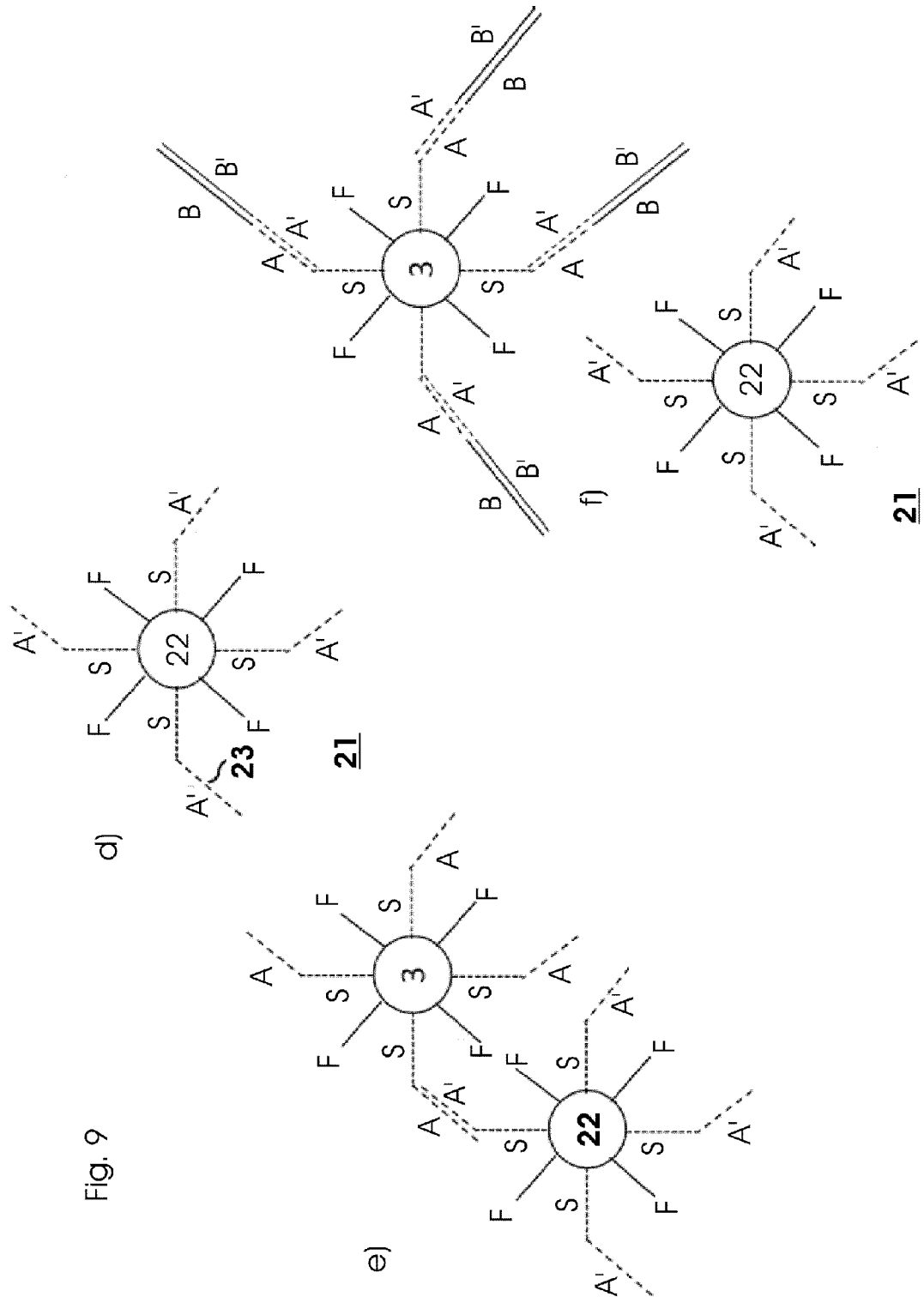

One possibility to verify the achieved amplification is shown in FIG. 9. FIGS. 9a and 9c outline the exponential amplification using a dissolved reverse primer 7 B' as already shown in FIG. 1a to 1h. After that, the test probes 21 are added to the sample 11. In this embodiment, the test probes 21 consist of second nanoparticles 22, which are functionalised on their surface with optional filling molecules 9 and the test sequence A', as shown in FIG. 9d. Optionally, a spacer sequence 6 S, which is not necessarily identical to the spacer sequence 6 S on the first nanoparticles 3 from FIG. 1 or FIG. 9a, can be placed between the test sequence A' and the surface of the second nanoparticles 22. The test sequence A' is complementary to at least a part of the primer sequence 5 A on the first nanoparticles 3. The test sequence A' competes for the primer sequence 5 A with the copies of the original 12 containing the partial sequence A' produced in the method in FIG. 1a to 1h. This means if many copies of the original 12 are present then the primer sequences 5 A on the surface of the first nanoparticles 3 are already occupied with the partial sequences A' of the copies of the original 12. In this case, the primer sequences 5 A cannot hybridise or can only hybridise to a limited extent to the test probes A' on the second nanoparticles 22. Thus, the first nanoparticles 3 are not connected or only connected to a limited extent to the second nanoparticles 22. As shown in FIG. 9c, the elongated primer sequences 5 A on the first nanoparticles 3 are hybridised with the original 12 and its copies and thus form rigid, double-stranded DNA which can pose a steric hindrance; due to this, also, a connection of the first nanoparticles 3 to the second nanoparticles 22 is prevented when a high number of copies of the original 12 are present. In the absence or presence of a small number of the original 12 and copies of the original 12, the first nanoparticles 3 are predominantly present with unoccupied primer sequences 5 A, as is shown in FIG. 9b. When the test probes 21 are added, the second nucleotide 23 A' hybridises to the unoccupied primer sequences 5 A on the first nanoparticles 3. Due to this, the first nanoparticles are connected to the second nanoparticles 22, as shown in FIG. 9e. In this embodiment, the extent of the connection of the first nanoparticles 3 to the second nanoparticles 22 is the weaker, the more copies of the original 12 have been produced by the amplification reaction, which depends on the concentration of the original 12 at the start of the amplification reaction. The buffer- and hybridisation conditions (e.g. temperature, salt concentration, nanoparticle concentration, concentrations of further buffer additives, pH) are chosen such that after completed specific extension of the primer sequence 5 A and completed synthesis of copies of the original 12 the suppression of the hybridisation of the primer sequences 5 A with the second oligonucleotide 23 A' is as efficient as possible. At the same time, the said conditions are chosen such that when no amplification has taken place, an efficient hybridisation of the primer sequences 5 A with the second oligonucleotides 23 A' is created. The connection of the first nanoparticles 3 with the second nanoparticles 22 resulting from the hybridisation can be verified by, e.g., a red shift and broadening of the plasmon resonance in the absorbance spectrum or by measuring the transmission change at one or several wavelengths after optothermal excitation of the nanoparticles 8 and the resulting denaturation of the nanoparticle linking DNA. Alternatively, the verification or a quantification of the copies of the original 12 produced in the method can be performed, e.g., by PCR, real-time PCR, quantitative real-time-PCR, gel-electrophoresis or by using dye labelled probes.

In the embodiment of the method shown on FIG. 9, first nanoparticles 3 made of gold and with a diameter of 60 nm are functionalised with oligonucleotides 4 as already shown in the embodiment in FIG. 6, the ratio of oligonucleotide 4 ID1 to oligonucleotide 4 ID2 in FIG. 9, however, is 1:9. After functionalisation and six washing steps, the first nanoparticles 3 are present in a concentration of 200 pM in a PBS buffer (20 mM PBS, 10 mM NaCl, 0.01% Tween 20, 0.01% azide, 1 mM EDTA, pH 7.5). The amplification reaction is carried out in a total volume of 10 µl in 200 µl sample tubes 24 (5 µl DreamTaq PCR Mastermix 2× (fermentas), 0.1 µl NaCl 5 M, 0.1 µl MgCl$_2$ 250 mM, 0.1 µl MgSO$_4$ 250 mM, 1 µl of the functionalised first nanoparticle 3 200 pM, 1 µl reversed primer ID6 500 nM, 1 µl oligonucleotide 4 ID3 (as original 12 to be amplified, wherein the concentration of the original 12, which is to be determined in the total volume of 10 µl, amounts to, e.g., 0 pM or 10 pM) solved in water with 100 nM oligonucleotide 4 ID4 (herein, oligonucleotide 4 ID4 serves the saturation of surfaces, e.g., during storage of the original 12 before the reaction), 1.7 µl water). The sample tubes 24 are kept at a temperature of 54° C. in a glass cuvette 25 in a water bath 26, as shown in FIG. 7.

Figure 10:
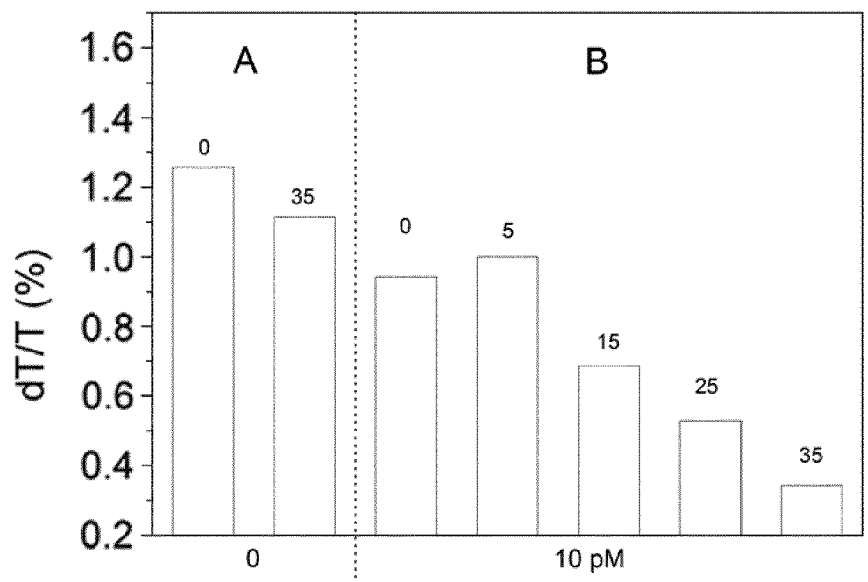
FIG. 10 shows in two diagrams the results of amplification reactions with global and local heating with test probes for the negative detection of DNA.
Figure 10:
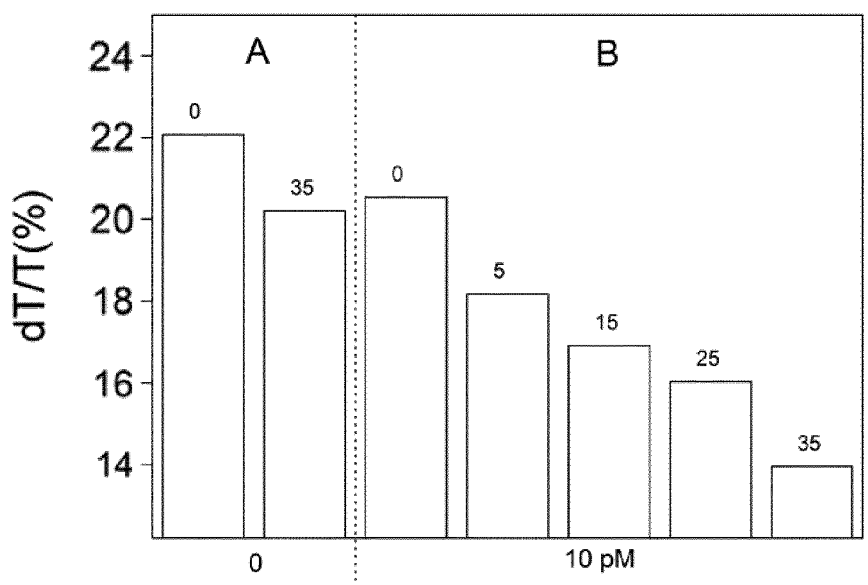

In this, 54° C. constitutes the annealing temperature as well as the elongation temperature. The water bath 26 serves, in addition to the temperature control, also to better couple the laser 16 into the non-planar surface of the sample tubes 24. The water in the water bath 26 permits for the difference in the refractive index between the outside and the inside of the sample tube 24 filled with the PCR reaction mixture to be reduced and thus to supress a refraction of the laser beam and a resultant negative influence on the focus quality and sharpness. Thereby, advantageously, the coupling of the laser 16 is improved. The laser 16, which serves to excite the nanoparticles 8, is frequency doubled diode-pumped Nd:YAg-Laser (Coherent Verdi V10), which is focussed at an output power of 3 W with an F-theta-lens (Jenoptik, focal distance 100 mm) behind a mirror scanner 18 into the sample tubes 24 in the water bath 26. The mirror scanner 18 permits for the focus to be moved row by row through the sample tubes 24, as shown in FIG. 3 and thus to involve the entire reaction volume 2 in the optothermal amplification. Per sample tube 24, 400 rows with a distance auf approximately 12 µm are scanned with the focus at a row-velocity in the sample tube 24 of approximately 2 m/s. This corresponds to one cycle in the first sample tubes 24. Subsequently, all other sample tubes 24 are scanned one after the other such that each sample tube 24 has experienced one cycle. After a waiting period of 40 s after the scanning of the first sample tube 24, the next cycle is started, this is repeated according to the predetermined number of cycles. 7 sample tubes 24 are examined, which are shown in FIG. 10*a* from left to the right. The first and second sample tube 24 do not contain any original 12. In the third till seventh sample tube 24, 10 pM of the original 12 are present as an initial concentration. As a control, the first and third sample tubes 24 are not treated optothermally. The fourth sample tube 24 was treated with 5 cycles, the fifth sample tube 24 with 15 cycles and the sixth sample tube 24 was treated with 25 cycles optothermally. The second and seventh sample tube 24 were treated with the maximum number of 35 cycles optothermally. All sample tubes 24 are inside the water bath 26 for the same amount of time, only the optothermal excitation differs. After the second and seventh sample tube 24 have completed all 35 cycles, all seven sample tubes 24 are removed from the water bath 26. One advantage of the method is that without great effort, different samples 11 can be treated with a different number of cycles, this can, e.g., be applied in a parallelised quantitative PCR.

The test probe 21 serves to determine the effect of the laser cycles and the concentration of the original 12, which test probe 21 can—under the chosen primer- and hybridisation conditions—preferably hybridise to the first nanoparticles 3 functionalised with primer sequences 5, which nanoparticles are not blocked by complementary copies of the original 12, which copies were produced in the amplification reaction. This corresponds to the test probe 21 as shown in FIG. 9. To produce the test probe 21, second nanoparticles 22 made of gold and with a diameter of 60 nm were functionalised with oligonucleotides 4 (according to J. Hurst, supra). In this, four parts oligonucleotide 4 ID2 and one part oligonucleotide 4 ID7 are used. After functionalisation and six washing steps, the second nanoparticles 22 were present at a concentration of 200 pM in a PBS buffer (20 mM PBS, 10 mM NaCl, 0.01% Tween 20, 0.01% azide, 1 mM EDTA, pH 7.5). For the hybridisation, a modified phosphate buffer was used (13 mM PBS, 200 mM NaCl, 0.02% Tween 20, 1 mM EDTA, 20 mM sodium citrate, 1 µg/ml PVP10, pH 7.5). 10 µl hybridisation solution contain 5.75 µl of the modified phosphate buffer, 1.5 µl formamide, 0.25 µl of the 200 pM test probe solution and 2.5 µl of the corresponding PCR-solution of the optothermal amplification reaction, which contains the first nanoparticles 3. The detection of the connection between the first nanoparticles 3 and the second nanoparticles 22 occurs by optothermal excitation of the nanoparticles 8, as described in FIG. 8*a*. FIG. 10*a* shows the change in transmission, which is produced by the laser pulse and the resultant dehybridisation of DNA between the first nanoparticles and second nanoparticles 22 and which transmission change is a measure for the presence of gold-DNA-gold-bonds in the sample 11. Shown in FIG. 10*a* on the left side in the section A are the first and the second sample tubes 24, which each contain no original, wherein the first simple tube 24 has completed none and the second simple tube 24 has completed 35 optothermal cycles. Both sample tubes 24 show a high measured transmission change as an indicator for a high measure of gold-DNA-gold-bonds. Without original 12, the different number of completed cycles thus has, in this case, no influence on the transmission change measured or on the measure of gold-DNA-gold-bonds; this is because no original 12 was available for the amplification and thus no blockage of the primer sequences 5 by copies of the original 12 can take place.

FIG. 10*a* shows on the right side in the section B the third till seventh sample tube 24 with an increasing number of optothermal cycles in the amplification reaction at an initial concentration of the original 12 of 10 pM. Here, it is evident that the transmission change measured as an indicator for the gold-DNA-gold-bonds essentially decreases with an increasing number of completed optothermal cycles. This shows that the more copies of the original 12 are produced, the more cycles are completed. In this, it is noteworthy that at an initial concentration of the original 12 of 10 pM, twice as many first nanoparticles 3 as originals 12 are present in the sample 11. Each first nanoparticle 3 typically carries between 1000 and 10000 primer sequences 5. In the initial concentration of the original 12, thus, approximately 1 in 2000 primer sequences 5 are blocked, which does not lead to a significant suppression of the gold-DNA-gold bonds between the first nanoparticles 3 and second nanoparticles 22. An effective suppression of the gold-DNA-gold-bonds, as shown in FIG. 10*a* with an increasing optothermal number of cycles, is only possible through a considerable amplification of the low initial concentration of the original 12.

FIG. 10*b* shows in an alternative detection method the concentration of the copies of the original 12 after the amplification reaction. In this, the samples 11 from the seven sample tubes 24 from FIG. 10*a* are first diluted 50-fold in water and subsequently a real-time PCR is carried out, which allows for the quantitative detection of the copies of the original. To this end, a real-time PCR solution is used, wherein 10 µl contain 5 µl 2× Phusion Blood PCR-buffer (including dNTPs and $MgCl_2$; Biozym), 0.2 µl Phusion Blood polymerase, 1 µl SybrGreen I (10×; Roche), 1 µl primer ID8 5 µM and 1 µl primer ID8 5 µM, 0.8 µl $H_2O$ and 1 µl of the 50-fold diluted sample 11. For the real-time PCR, at first a denaturation at 98° C. is carried out for 1 minute, subsequently, 40 cycles are completed, which each consist of 1 second at 98° C., 5 seconds at 66° C. and 1 second at 72° C. The fluorescence of the SybrGreen I is measured at the end of each annealing phase at 66° C. For the real-time PCR, a Stratagene Mx3005P by Agilent Technologies was used. On the y-axis in FIG. 10*b*, the threshold cycle (Ct-value) of the real-time PCR is shown, in which the copies of the original have reached a predetermined concentration for the first time. The higher the concentration of the copies of the original 12 at the start of the real-time PCR, the smaller is the threshold cycle. The results in FIG. 10*b* confirm the results from 10*a*: the more optothermal cycles are completed at a given initial concentration of the original 12, the higher is the number of copies of the original 12 after the amplification reaction.

Preferably, in the optothermal denaturation, only small partial volumes of the sample 11 are heated such that it is also possible to use non-thermostable DNA polymerases 10. In one embodiment, the Klenow fragment 29, which is not thermal-stable, is used as DNA polymerase. The Klenow fragment 29 has the advantage that it is more salt tolerant in the amplification reaction. Thereby, preferably better reaction conditions can be chosen in detection reactions with first nanoparticles 3 and second nanoparticles 22, which can lead to better specificity and sensitivity of the detection reaction. In addition to this, the Klenow fragment 29 offers the advantage that at 76 kDA, it is smaller than the typically used Taq DNA polymerase with 95 kDA. Thus, in the closed proximity of nanoparticles 8 functionalised with oligonucleotides 4, the Klenow fragment 29 experiences less steric hindrance than the Taq DNA polymerase 10. Furthermore, the Klenow fragment 29 offers the advantage that its optimal elongation temperature is at 37° C. The elongation at 37° C. offers the advantage that a smaller thermal strain is exerted on the nanoparticles 8 and thus lower requirements for the stability of the nanoparticles 8 are necessary; at the same time there, is more flexibility in the use of potentially nanoparticle destabilizing salts. In this embodiment, in which the Klenow fragment 29 is used for amplification, first nanoparticles 3 made of gold with a diameter of 60 nm are functionalised at first in analogy to the method used in FIG. 1. Herein, the shorter primer sequence 5 ID9 is used, as at the lower annealing temperature and the higher salt concentrations a higher specificity in the hybridisation with the original 12 can be achieved. The ratio of oligonucleotide 4 ID9 to oligonucleotide 4 ID2 amounts to 1:9. After functionalisation and six washing steps, the first nanoparticles 3 are present in a concentration of 200 pM in a PBS buffer (20 mM PBS, 10 mM NaCl, 0.01% Tween 20, 0.01% azide, 1 mM EDTA, pH 7.5). The amplification reaction is carried out in 10 µl PCR mixture in 100 µl sample tubes (1 µl 10× reaction buffer for the Klenow fragment exo- (contains no dNTPs and no polymerase; fermentas), 0.2 µl Klenow fragment exo- (fermentas), 1 µl dNTPs, each 2.5 mM (fermentas), 0.2 µl NaCL 5M, 0.2 µl MgCl2 250 mM, 0.2 µl MgSO4 250 mM, 1 µl first nanoparticles 3 in a concentration of 200 pM, 1 µl reversed primer ID6 500 nM, 1 µl oligonucleotide ID3 as original 12 (herein, the original 12 is present in the PCR mixture at a concentration of, e.g., 0 pM, 10 pM or 20 pM), 4.2 µl water). The quantities of salt used herein are significantly higher than in the example from FIG. 10. With the DNA polymerase 10 from FIG. 10, no sufficient amplification would be possible in these salt concentrations. As shown in FIG. 7, the sample tubes 24 are temperature-controlled to 37° C. in a glass cuvette 25 in a water bath 26. The temperature of 37° C. is, herein, annealing temperature as well as elongation temperature. The laser 16 serves to excite the first nanoparticles 3 and is a frequency-doubled diode-pumped Nd:YAg laser (coherent Verdi V10), which is focussed into the sample tubes 24 in the water bath 26 at an output power of 1.5 W with a F-theta-lens (Jenoptik, focal distance 100 mm) behind a mirror scanner 18 (Cambridge Technologies, Pro Series 1). The mirror scanner 18 permits to move the focus through the sample tubes 24 row by row, as already shown in FIG. 3, and thus to involve the entire reaction volume 2 in the optothermal amplification. Per sample tube 24, 1000 rows are scanned with the focus at a distance of approximately 5 µm at a row velocity in the sample tube 24 of approximately 5 m/s. This corresponds to one cycle in the first sample tube 24. Subsequently, all the other sample tubes 24 are scanned one after the other such that each sample tube 24 has completed one cycle. After a waiting period of 40 s after the scanning of the first sample tube 24, the next cycle is started and this is repeated until each sample tube 24 has completed 35 cycles in total. From left to right in FIG. 11, the first three sample tubes 24 have received the said PCR mixture including Klenow fragment 29 and dNTPs. The sample tubes 24 four till six contain Klenow fragment 29, but no dNTPs and the sample tubes 24 seven till nine contain dNTPs, but no Klenow fragment 29. The sample tubes 24 one, four and seven contain no original 12, two, five and eight contain 10 pM original 12 and three, six and nine contain 20 pM original 12 as shown in the row below the diagram in FIG. 11. After all the sample tubes 24 have completed 35 cycles, they are removed from the water bath 26. A test probe 21 corresponding to the one from FIG. 9 is used in the analysis of the amplification reaction. For the hybridisation with the test probe 21, a modified phosphate buffer is used (13 mM PBS, 200 mM NaCl, 0.02% Tween 20, 1 mM EDTA, 20 mM sodium citrate, 1 µg/ml PVP10, pH 7.5). 10 µl hybridisation solution contain 3.35 µl of the modified phosphate buffer, 3.3 µl formamide, 0.6 µl NaCl 5M, 0.25 µl of the 200 pM test probe solution and 2.5 µl of the corresponding PCR solution after the amplification).

Figure 11:
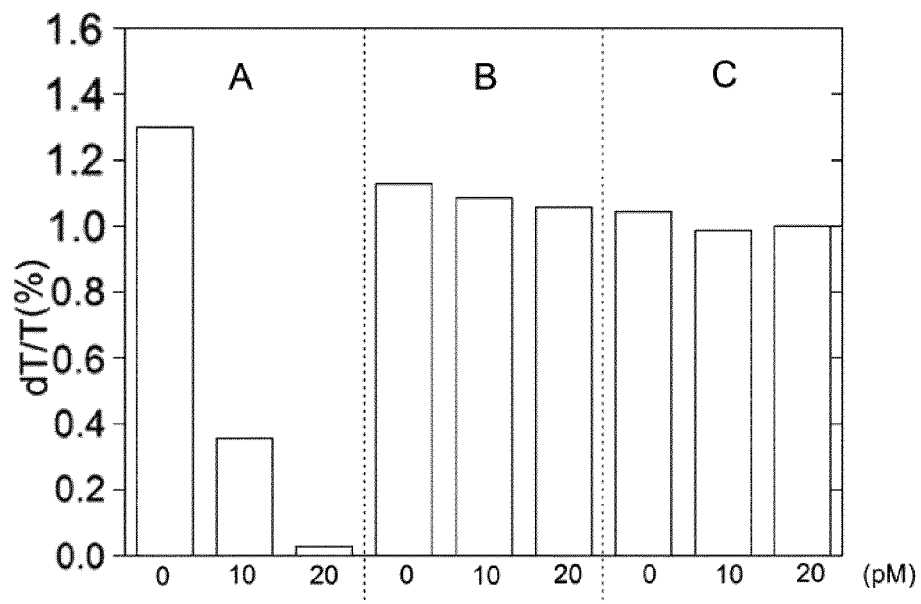
FIG. 11 shows in a diagram the results of amplification reactions with the non-thermostable Klenow fragment.

The verification of the connection of first nanoparticles 3 and test probes 21 is carried out by optothermal excitation of the nanoparticles 8. FIG. 11 shows the transmission change, which is produced by the laser pulse and the resultant dehybridisation of DNA between the nanoparticles 8 and which is a measure for the presence of gold-DNA-gold-bonds in the solution; the concentration of the original 12 before the reaction is shown below the diagram. On the left side of FIG. 11 in section A, the results for the sample tubes 24 one till three are shown, which contain the components Klenow fragment 29 and dNTPs required for the PCR. Here, it is evident that with an increasing amount of copies of the original 12, the transmission change measured as an indicator for the measure of gold-DNA-gold-bonds decreases. The non-thermal-stable Klenow fragment 29 can carry out an amplification of the original 12 in this embodiment, even though it does not tolerate high temperatures. As in the present optothermal amplification reaction, the sample 11 is only heated locally, the Klenow fragment 29 experiences only little thermal strain and can amplify the original 12 over many cycles without being destroyed. In FIG. 11 in the middle in section B, the results of the sample tubes 24 four till six, which contain no dNTPs, are shown. Here, no significant transmission change is detectable in any of the concentrations of the original 12 used. This means that no amplification has taken place. In section C in FIG. 11 on the right the results of the sample tubes 24 seven till nine is shown, which contain no Klenow fragment 29. Here, again, no amplification has taken place. This example shows that the non-thermostable Klenow fragment 29 can also be used in performing an amplification reaction.

Figure 12:
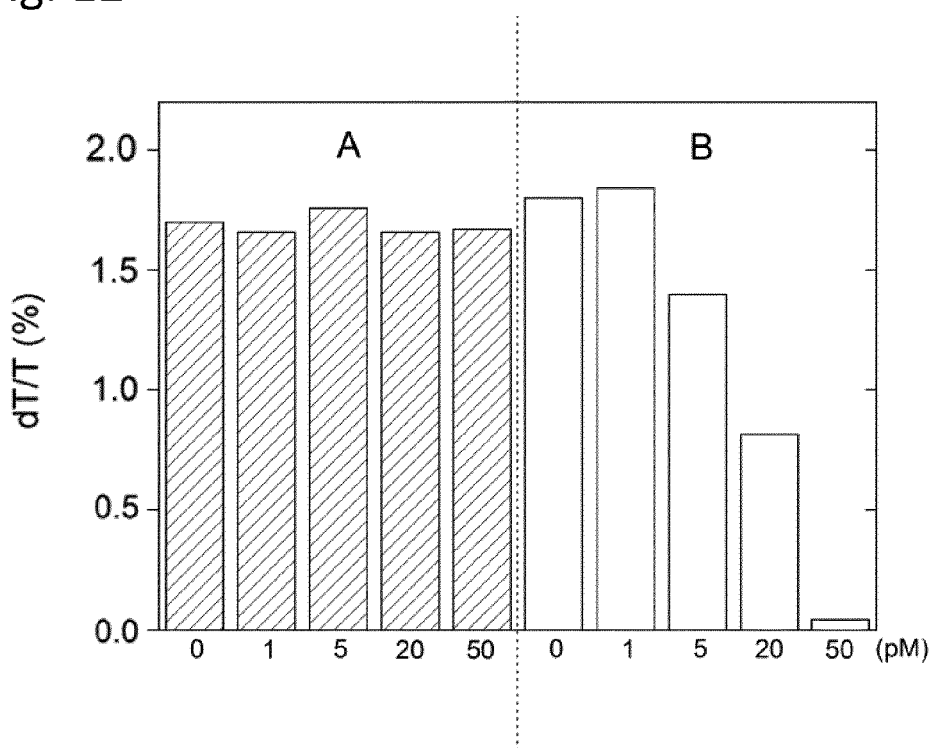
FIG. 12 shows in a diagram the results of amplification reactions with a fixed and a moving laser beam.

In the embodiment shown in FIG. 12, the optothermal amplification is shown depending on the movement of the laser beam through the reaction volume 2. In this, concentrations of the original of 0, 1, 5, 20 and 50 pM are chosen in the 100 µl sample tubes 24, as shown in the row below the diagram in FIG. 12. The sample tubes 24 are temperature-controlled to 60° C. in a glass cuvette 25 in a water bath 26 as shown in FIG. 7, wherein 60° C. is annealing temperature as well as elongation temperature. The optothermal heating is created by the laser 16, which consists of a frequency-doubled diode-pumped Nd:YAg laser (coherent Verdi V10), which is focussed into the sample tubes 24 in the water bath 26 at an output power of 3 W with a F-theta-lens (Jenoptik, focal distance 100 mm) behind a mirror scanner 18 (Cambridge Technologies, Pro Series 1). FIG. 12 shows on the left side in section A five sample tubes 24 with increasing concentrations of the original 12, which were each excited optothermally for one second, wherein the laser focus was resting in the middle of the reaction volume 2 without movement. After the first sample tube 24 was irradiated in this manner for one second, it is not irradiated for 40 s. This corresponds to one cycle in the first sample tube 24. During the waiting period of 40 s, the remaining sample tubes 24 complete the first cycle. The cycles are repeated 35 times in total. The detection of the hybridisation between nanoparticles 8, which contain primer sequences 5, and the test probes 21 is carried out by means of optothermal excitation of nanoparticles 8 as already shown in FIG. 10. As shown in FIG. 12 on the left side in section A, without movement of the laser focus, no influence of the concentration of the original 12 on the transmission change can be observed. This shows, that no significant amplification of the original 12 has taken place. The reason is that only a small fraction of the entire reaction volume 2 is in focus and only the nanoparticles 8 in this partial volume take part in the reaction. On the right side of FIG. 12 in section B, five sample tubes 24 are shown with increasing concentration of the original 12 from left to right, which sample tubes 24 were each excited for one second, wherein additionally, the laser focus was moved through the reaction volume 2. In this way, as already shown in FIG. 3, the entire reaction volume 2 is scanned row by row and thus involved in the optothermal reaction. In each sample tube 24, 1000 rows at a distance of approximately 5 µm are scanned with the focus at a row velocity in the sample tube 24 of approximately 5 m/s. This corresponds to one cycle in the first sample tube 24. Subsequently, the next sample tubes 24 are scanned one after the other, until all five sample tubes 24 are scanned. After a waiting period of 40 s measured from the scanning of the first sample tube 24, the next cycle is started and this is repeated 35 times. From FIG. 12 on the right in section B it is evident that with increasing concentration of the original 12, the transmission change measured decreases. This is an indication for the decreasing measure of gold-DNA-gold bonds. Only through the movement of the focus and at an unchanged laser power and duration of irradiation, amplification takes place as the movement of the focus involves a large part of the nanoparticles 8 in the sample 11 in the amplification reaction.

Figure 13:
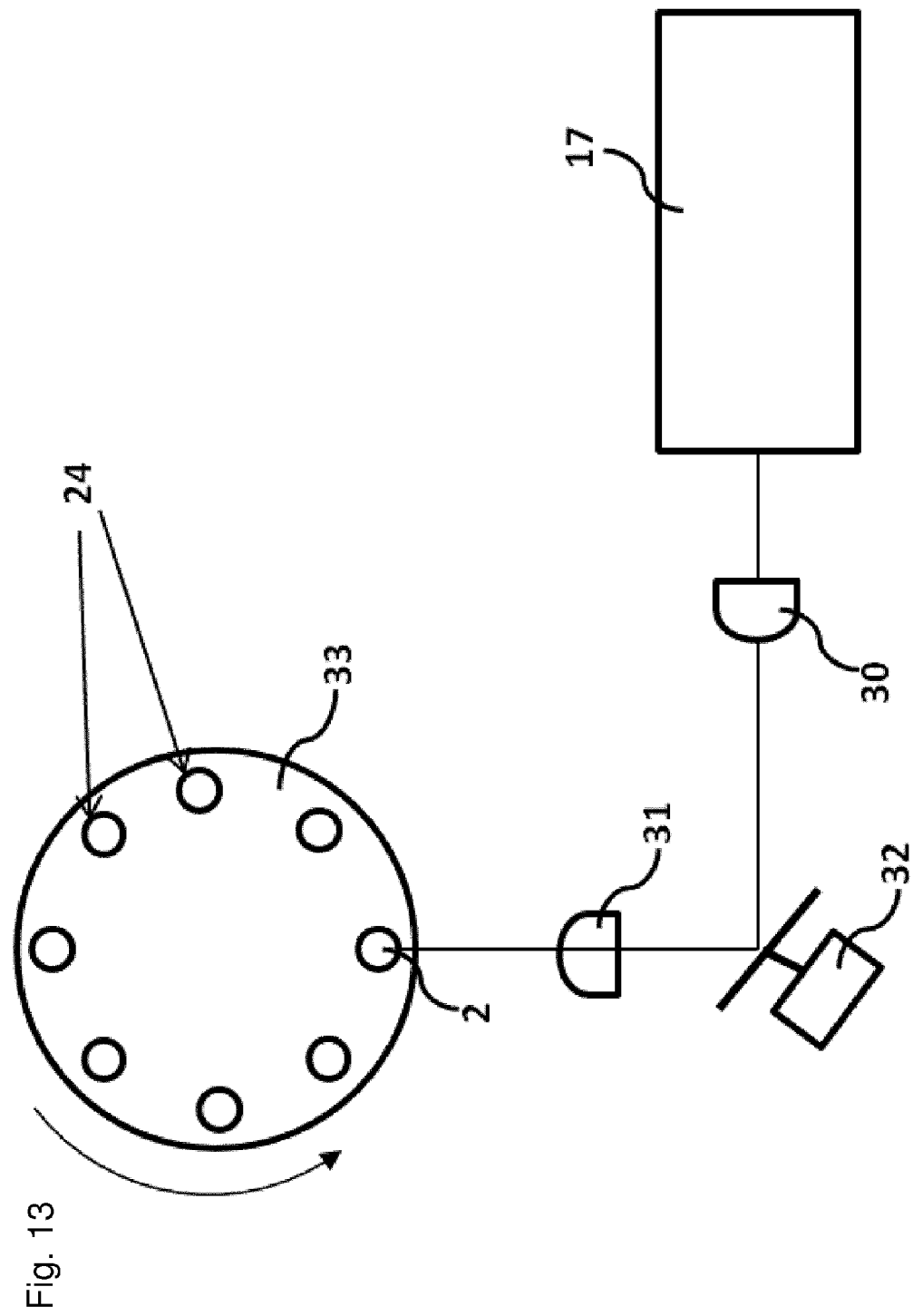
FIG. 13 shows in a schematic representation a setup for carrying out the method according to the invention with a light source, a deflecting element and a movable sample tube.

In FIG. 13, an apparatus for performing the method according to the invention is shown, wherein a light source 17 directs a light beam through an optional first objective 30 on a deflecting element 32, e.g., a mirror, and through an optional second objective 31 onto a sample tube 24. In this, the sample tube 24 is mounted on a rotatable unit 33 together with further sample tubes 24 such that by turning the unit 33, different sample tubes 24 can be illuminated at different times. Thus, advantageously, it is achievable to excite a large number of nanoparticles 8 present in the sample tubes 24, even with a light source 17 with a low power.

Figure 14:
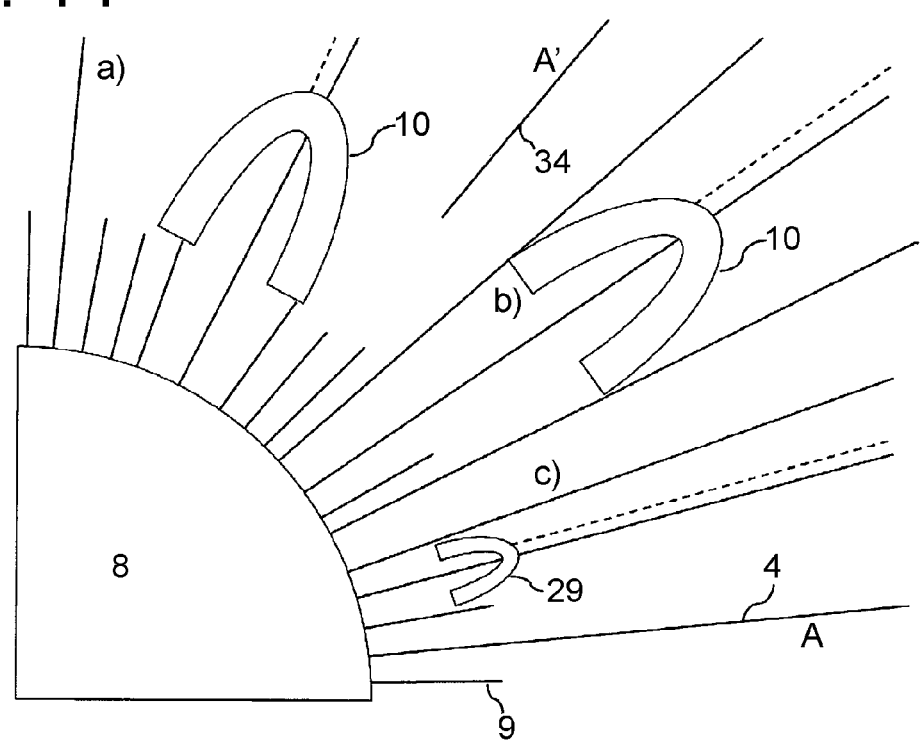
FIG. 14 shows in a schematic representation a section of a nanoparticle according to the invention with filling molecules, oligonucleotides and DNA polymerases.

FIG. 14 shows a section of a nanoparticle 8 according to the invention which contains filling molecules 9 and oligonucleotides 4 on its surface. Conventional DNA polymerases 10 synthesise a complementary strand (dashed) along the oligonucleotides 4. During this, the large, conventional DNA polymerases 10 experience steric hindrance through the filling molecules in FIG. 14a. In FIG. 14b, the DNA polymerases 10 experience steric hindrance by neighbouring oligonucleotides 4. The steric hindrance in FIGS. 14a and 14b can each lead to premature strand break of the newly synthesised strand. The Klenow fragment 29 in FIG. 14c can—as it is smaller than the conventional DNA polymerases 10—reach through between the filling molecules 9 and the oligonucleotides 4 and can thus finish synthesising the new strand till the end. Even if the Klenow fragment 29 cannot reach through the filling molecules, the Klenow fragment 29 can still reach closer to the sterically hindering filling molecules 9 with its active centre, thus a potential strand break of the newly synthesised strand occurs only later. Hence, smaller polymerases enable the more effective use of primer sequences close to particle surfaces. Additionally, the locally produced heat can be used particularly effectively for the denaturing step in close proximity of the nanoparticle surface. In addition to this, a counter sequence 34 with the sequence A' is shown. The counter sequence 34 is complementary to a oligonucleotide 4 with the sequence A on the nanoparticle 8 and serves to neutralise oligonucleotides 4 with the sequence A, which unintentionally detach from the nanoparticles 8, such that the oligonucleotides 4 cannot act as free primers 7.

Figure 15:
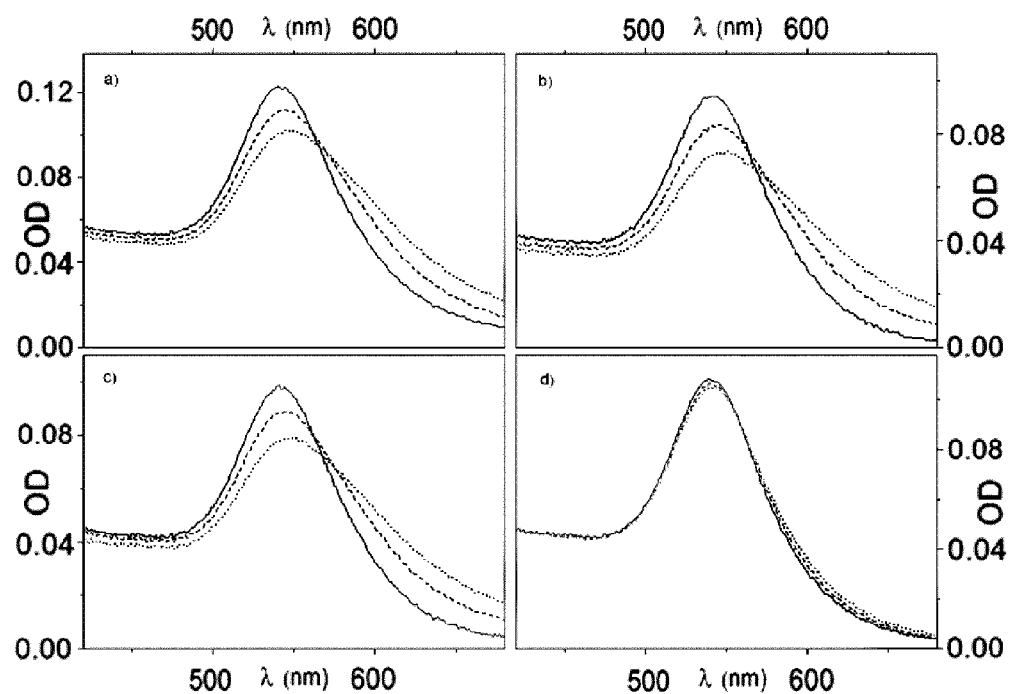
FIG. 15 shows in four diagrams the results of amplification reactions with test probes for the negative detection of DNA.

In the embodiment in FIG. 15, the optothermal amplification using nanoparticle oligonucleotide-conjugates is shown, wherein the covalent bond between first nanoparticles 3 and primer sequences 5 is carried out with two thiols. To this end, first nanoparticles 3 made of gold with a diameter of 60 nm are functionalised with oligonucleotides 4 (according to J. Hurst, supra). In this, oligonucleotides 4 ID10 (IDT Technologies, Inc.) are used, which compared to oligonucleotide ID1 carry a dithiol instead of a thiol on their 5'-end. After functionalisation and six washing steps, the first nanoparticles 3 are present at a concentration of 200 pM in a PBS buffer (20 mM PBS, 10 mM NaCl, 0.01% Tween 20, 0.01%, azide 1 mM EDTA, pH 7.5). The amplification reaction is performed in a total volume of 10 µl in 200 µl sample tubes 24 (5 µl DreamTaq PCR Mastermix 2× (fermentas), 0.1 µl NaCl 5M, 0.1 µl $MgCl_2$ 250 mM, 0.1 µl $MgSO_4$ 250 mM, 1 µl of the functionalised first nanoparticles 200 pM, 1 µl reversed primer ID6 500 nM, 1 µl oligonucleotide 4 ID3 (as original 12 to be amplified) dissolved at a concentration of 0 or 200 pM, respectively, in water with 100 nM oligonucleotide 4 ID4 (herein, oligonucleotide 4 ID4 serves to saturate surfaces, e.g., during the storage of the original 12 before the reaction), 1.7 μl water). As shown in FIG. 7, the sample tubes 24 are temperature controlled to 60° C. in a glass cuvette 25 in a water bath 26, which is annealing temperature as well as elongation temperature. The first two sample tubes 24 are inserted into the water bath as negative controls, but are not hit by the laser beam. Initial concentrations of the original 12 are chosen to be 0 pM in the first sample tube 24 and 20 pM in the second sample tube 24. The third and fourth sample tube is treated optothermally. The optothermal heating is performed by the laser 16, which consists of a frequency-doubled diode-pumped Nd:YAg laser (Coherent Verdi V10), which is focussed into the sample tubes 24 in the water bath 26 at an output power of 3 W with a F-theta-lens (Jenoptik, focal distance 100 mm) behind a mirror scanner 18 (Cambridge Technologies, Pro Series 1). For each sample tube 24, 500 rows are scanned with a distance of approximately 10 μm with the focus at a row velocity in the sample tube of approximately 5 m/s. This corresponds to one cycle in the third sample tube 24. Subsequently, the fourth sample tube 24 is scanned such that third and fourth sample tube have completed one cycle. After a waiting period of 40 s after the scanning of the third sample tube 24, the next cycle is started and this is repeated until third and fourth sample tube 24 have each completed 35 cycles. As initial concentration of the original 12, 0 pM is chosen for the third sample tube 24 and 20 pM is chosen for the fourth sample tube 24. After the third and fourth sample tube have completed 35 cycles, all four sample tubes 24 are removed from the water bath 26. A test probe 21 serves to examine the effect of the laser cycles and the concentration of the original 12, which test probe 21 is preferably able to hybridise under the primer and hybridisation conditions chosen to the first nanoparticles 3 functionalised with primer sequences 5, which first nanoparticles 3 are not blocked by complementary copies of the original 12, which were produced in the amplification reaction. This corresponds to the test probe 21 as shown in FIG. 9. The production of the test probe 21 and the hybridisation conditions were already described in FIG. 10. The diagrams in FIG. 15 show absorbance spectra of the hybridisation solution, which contains the test probe 21 as well as the corresponding PCR solution from the optothermal amplification reaction, which contains the first nanoparticles 3. The absorbance spectra were recorded in a quartz cuvette with a 3 mm optical path in a Varian Cary 50 spectrometer. In the diagrams the solid line shows the absorbance spectrum immediately after mixing the PCR solution and the optothermal amplification reaction, which contains the first nanoparticles 3 with the test probe 21; the dashed line is recorded 6 minutes after hybridisation and the dotted line after 12 minutes hybridisation. In FIG. 15*a*, shown are the spectra during the hybridisation of the test probe 21 with the nanoparticles 8 of the PCR product from the first sample tube, which contained no original 12 before the amplification reaction and which experienced no optothermal treatment. A clear red shift and broadening of the plasmon resonance of the nanoparticles 3 is seen with increasing hybridisation time as a hybridisation between test probes 21 and primer sequences 5 takes place on the first nanoparticles 3. A comparable hybridisation can also be seen in FIG. 15*b*, which shows the hybridisation of the test probe 21 with nanoparticles 8 of the PCR product from the second sample tube, which contained 20 pM original 12 before the amplification reaction and has received no optothermal treatment. A comparable hybridisation can also be seen in FIG. 15*c*, which shows the hybridisation of the test probe 21 with the nanoparticles 8 of the PCR product from the third sample tube, which contained no original 12 before the amplification reaction, but received a optothermal treatment. The hybridisation in FIG. 15*c* shows that primer sequences 5 are still bound to the first nanoparticles 3 after optothermal treatment. Only in FIG. 15*d*, which shows the hybridisation of the test probe 21 with nanoparticles 8 of the PCR product from the fourth sample tube, which contained 20 pM original 12 before the amplification reaction and received an optothermal treatment, almost no change of the absorbance spectra is seen with increasing hybridisation time. Only in the latter case, a sufficient number of copies of the original 12 were produced during the amplification reaction, which copies now block primer sequences 5 on the first nanoparticles 3 and thus prevent a hybridisation with the test probes 21. This example shows that the optothermal amplification reaction also functions if primer sequences 5 are bound covalently to dithiols on the surface of the first nanoparticles 3 and that absorbance spectra for the detection of the concentration of the copies of the original 12 can be used after the amplification reaction.

The features disclosed in the present description, the claims and the drawings can be of relevance individually as well as in any combination for the realisation of the invention in its various embodiments.

REFERENCE NUMBER LIST

1 nucleic acid
2 reaction volume
3 first nanoparticles
4 oligonucleotide
5 primer sequence
6 spacer sequence
7 primer
8 nanoparticle
9 filling molecule
10 DNA polymerase
11 sample
12 original
13 complement
14 forward primer
15 reverse primer
16 laser
17 light source
18 mirror scanner
19 mirror
20 first oligonucleotide
21 test probe
22 second nanoparticle
23 second oligonucleotide
24 sample tube
25 glass cuvette
26 water bath
27 first laser
28 second laser
29 Klenow fragment
30 first objective
31 second objective
32 deflecting element
33 rotatable unit
34 counter sequence
35 photo diode

The invention claimed is:

1. A method for the amplification of nucleic acids comprising amplifying the nucleic acids, wherein the amplification comprises one or more heating steps, and a step of providing nanoparticles with the nucleic acids in a reaction volume, wherein the heating in at least one heating step is achieved at least partially through excitation of the nanoparticles so that the nanoparticles transfer heat to their environment through the excitation, wherein through the excitation of the nanoparticles, the environment of the nanoparticles is heated locally, wherein the interval of the excitation is chosen to be shorter or equal to a critical excitation time $t1=(s1*|x|)^2/D$, and wherein $s1=100$, $|x|$ is the mean nanoparticle distance, and D is the thermal diffusivity of the medium between the nanoparticles.

2. The method according to claim 1, wherein the nucleic acids are amplified by a polymerase chain reaction.

3. The method according to claim 1, wherein the nanoparticles are excited by a laser.

4. The method according claim 1, wherein the nanoparticles are conjugated with oligonucleotides.

5. The method according claim 4, wherein one kind of conjugates of the nanoparticles and the oligonucleotides is conjugated with forward primers as well as reverse primers.

6. The method according to claim 4, wherein in the method, counter sequences are used, which can bind to the oligonucleotides, which have detached from the nanoparticles, to which the oligonucleotides had been attached previously.

7. The method according to claim 4, wherein filling molecules are attached to the nanoparticles.

8. The method according to claim 4, wherein the oligonucleotides on the nanoparticles contain a spacer sequence as a partial sequence.

9. The method according to claim 4, wherein the heat, which is transferred to the environment of the nanoparticles by the excitation of the nanoparticles, is sufficient to dehybridise the oligonucleotides on the surface of the nanoparticles from nucleic acids hybridised with the oligonucleotides.

10. The method according to claim 1, wherein the method further comprises a global heating step.

11. The method according to claim 1, wherein the method further comprises an annealing step and the annealing temperature is equal to an elongation temperature.

12. The method according to claim 1, wherein at any one time during the method only a part of the nanoparticles is heated by excitation.

13. The method according to claim 1, wherein the method further comprises a directed movement of the sample relative to an exciting field takes place such that at different times, nanoparticles in different partial volumes of the sample are excited.

14. The method according to claim 1, wherein the method further comprises use of a thermolabile DNA polymerase.

15. The method according to claim 1, wherein the method further comprises concentration of the amplification product and the concentration of the product of the amplification reaction is determined using test probes.

* * * * *